United States Patent [19]
Zimmerman et al.

[11] Patent Number: 6,093,400
[45] Date of Patent: *Jul. 25, 2000

[54] MODIFIED HGP-30 PEPTIDES, CONJUGATES, COMPOSITIONS AND METHODS OF USE

[75] Inventors: Daniel H. Zimmerman, Bethesda; Prem S. Sarin, Gaithersburg, both of Md.

[73] Assignee: Cel Sci Corporation, Denver, Colo.

[*] Notice: This patent issued on a continued prosecution application filed under 37 CFR 1.53(d), and is subject to the twenty year patent term provisions of 35 U.S.C. 154(a)(2).

[21] Appl. No.: 08/695,301

[22] Filed: Aug. 9, 1996

[51] Int. Cl.⁷ ...................................................... A61K 39/21
[52] U.S. Cl. ................................... 424/188.1; 424/184.1; 530/324; 530/861
[58] Field of Search .............................. 424/184.1, 188.1; 530/324, 861

[56] References Cited

U.S. PATENT DOCUMENTS 4,983,387  1/1991  Goldstein et al. .

FOREIGN PATENT DOCUMENTS

89/12458  of 0000  WIPO .

OTHER PUBLICATIONS

Sarin, P. S. et al. Cellular and Molecular Biology 41 (3): 401–407, May 1995.
Bomford, R. et al. AIDS Research and Human Retroviruses 8 (10): 1765–1771, Oct. 1992.
Clerici, M. et al. Immunology Today 15 (12): 575–581, Dec. 1994.
Finkelman, et al., Ann Rev Immunol 8:303 (1990).
Snapper, et al., Science 236:944 (1987).
Salgame, et al., Science 254:279 (1991).
Romagnani, Immunol Today 13:379 (1992).
Bretsher, et al., Science 257:539 (1992).
Cox, et al., Immunol Today 13:445 (1992).
Mosmann, et al., Ann Rev Immunol 7:145 (1989).
Taylor–Robinson, et al., Science 260:1931 (1993).
Khalife, et al., AIDS Res and Hu Retro 4:3 (1988).
Wicker, et al., Eur. J. Immunol. 14:442 (1984).
Zimmerman, et al., Vaccine Res. 5:91 (1996).
Zimmerman, et al., Vaccine Res. 5:103 (1996).
McDougal, et al., J. Clin. Invest. 80:316 (1987).
Jiang, et al., J. AIDS 5:382 (1992).
Broliden, et al., Clin. Expt. Immunol. 76:216 (1989).
Ljunggren, et al., J. Immunol. Meth 104:7 (1987).
Ljunggren, et al., Clin. Exp. Immunol. 73:343 (1987).
Shakib, F., Ed., "The Human IgG Subclasses: Molecular Analysis of Structure, Function, and Regulation" Jeffries, et al, Chapt. 6, p. 93; Pound, et al., Chapter 7, p. 111; Weiner, Chapter 8, p. 135 (1990).
Rook, et al., J. Immunol 138:1064 (1987).
Mosier, et al., Science 251:791 (1991).
Mosier, et al., AIDS Res. Hu. Retro., 8:1387 (1992).
Papsidero et al., J. Virol. 63:267 (1989).
Boucher, et al., Clin. Lab. Anal. 4:43 (1990).
Mosier, et al., Proc. Nat. Acad. Sci. 90:2443 (1993).
Parren, et al., AIDS 9(6):F1–6 (1995).
Sarin, et al., Science 232:1135 (1986).
Naylor, et al., Proc. Nat. Acad. Sci. 84:2951 (1987).
Gazzard, et al., Vaccine Res. 1:129 (1992).
Sarin, et al., Vaccine Res. 3:49 (1994).
Kahn, AIDS Res. Hu. Retroviruses 8:1321 (1992).
Naylor, et al., Int. J. Immunopharm 13(Suppl):117 (1991).
Sarin, et al., Cell Molec. Biol. 41:401 (1995).
Kahn, et al., Abstract 13, International AIDS Conference, Vancouver, Canada, Jul. 1996.
Talmadge, et al., Clin. Immunol., Meeting, New Orleans, LA, Jun. 1996.
Willer, et al., Biomed & Pharmacol. 46:359 (1992).
Kawano, et al., J. Immunol. 153:4948 (1994).
Lundgren, et al., Eur. J. Immunol. 19:1311 (1989).
Bird, et al., Immunol. 69:335 (1990).
Hadjipetrou–Kourounakis, et al., Scan. J. Immunol. 19:219 (1984).
Kenney, et al., J. Immunol. Meth. 121:157 (1989).
van de Wihgert, et al., Infect. Immun. 59:2750 (1991).
Golding, et al., Am. J. Trop. Med. Hyg. 50(4):suppl:33 (1994).
Lachman, et al., AIDS Res. Hu. Retroviruses 11(8):921 (1995).
Bui, et al., J. AIDS 7:799 (1994).
Sercarz, et al., Immunol. Today 12:111 (1991).
Yowell, et al., Nature, 279:70 (1979).
Naylor, et al., Mono. Viro. 18:74 (1990).
Coates, et al., Nature 326:549 (1987).
Wahren, et al., J. AIDS 4:448 (1989).

*Primary Examiner*—Jeffery Stucker

[57] ABSTRACT

An antigenic peptide fragment from the p17 gag protein of HIV includes a portion from HGP-30 and a contiguous portion from HGP-35 such that the peptide fragment is capable of inducing a TH1 immune response when administered to a person suffering from AIDS or at risk for AIDS. The peptide has from about 25 to about 37 amino acids, such as, for example, the sequence

ATL YSV HQR IDV KDT

KEA LEK IEE EQN KS    SEQ ID NO: 5.

18 Claims, No Drawings

MODIFIED HGP-30 PEPTIDES, CONJUGATES, COMPOSITIONS AND METHODS OF USE

BACKGROUND OF INVENTION (1) Field of the Invention

This invention relates to peptide fragments derived from the p17 gag protein of human immunodeficiency virus (HIV) which is the causative organism of the disease known as Acquired Immune Deficiency Syndrome (AIDS). The invention relates to the use of these p17 peptide fragments and analogues as a component of an AIDS vaccine and to the resulting AIDS vaccine compositions which are capable of eliciting TH1 associated antibodies and other aspects of a TH1 immune response.

(2) Discussion of the Prior Art

There has been extensive research over the past several years, first to identify the cause of AIDS and after the positive identification of the retroviruses generically referred to as HIV, as the causative organism, efforts have concentrated on more detailed analysis of the genetic makeup, molecular biology, pathogenesis, biochemistry, development of highly sensitive methods of detection of virus and antibodies and treatments, and therapies. Extensive progress has been made in all of these areas yet much work needs to be done to effectively combat the spread of AIDS. An essential part of the approach for combatting the spread of the highly infectious HIV virus is the development of effective vaccines that stimulate the appropriate components of the immune system. In this regard, knowledge of natural history of infection with HIV and the various immune responses and the clinical condition and the outcome may be useful in preparing effective vaccine preparations for either therapeutic or preventive means. In this regard accurate diagnosis of the stage of disease and the immune status with regard to HIV and the knowledge that certain means are available may encourage infected patients to alter or modify their lifestyles in such manner as to reduce the risk of spreading the virus. Additionally, identification of protective antibodies based on epitope recognition can offer a more effective mechanism for staging and/or diagnosing the AIDS or pre-AIDS disease. Such staging and early diagnosis of seropositive individuals may then allow for vaccinations to provide the appropriate protective immune responses for treating the seropositive individual.

For many infectious diseases it is now recognized that the presence or absence of antibody is not as critical in the satisfactory clearance of the agent and disease resolution as much as it is the class or subclass of antibody, other immune system activities such as cytotoxic T lymphocytes and the particular antigens of the agent being recognized. For example, resolution of intracellular infections, such as tuberculosis, require activation of delayed-type hypersensitivity (DTH) and helper T cell activities, properties of CD4+ T cells (Finkelman et al. 1990, Ann Rev Immunol 8:303). CD4+ T helper cells have been delineated into TH1 and TH2 subsets in the mouse based on the cytokines produced and other activities which are promoted or associated with the T cell (Snapper et al 1987, Science 236:944; Salgame et al 1991, Science 254:279; Romagnani 1992, Immunol Today 13:379). In the mouse TH1 cells promote DTH, produce IL-2, interferon-γ and promote IgG2a synthesis whereas TH2 cells produce IL-4, IL-10, promote B cell growth and differentiation leading to IgG1 and IgE production (Bretsher et al 1992, Science 257:539). CD8+ cytotoxic T cell responses are also associated with TH1 responses (Cox et al. 1992 Immunol Today 13:445). Based upon this information the nature of the T cell response generated by a specific immunization protocol can be evaluated by measurement of the specific lymphokine and/or antibodies produced by the individual (Finkelman et al. 1990, Annu Rev Immunol 8:303; Mosmann et al. 1989, Ann Rev Immunol 7:145). More recently it has been recognized that CD8+ cells responsible for CTL activity form a part of the cellular immune response mediated by TH1 cells (Taylor-Robinson et al. 1993,Science 260:1931).

HIV has several major classes of proteins referred to as the outer envelope structural group (env gp120 and p41), gag (or internal structural proteins p24, p17) and several nonstructural and regulatory genes and encoded proteins. Examination of the immune response and the disease state can be of assistance in designing new agents as vaccines. In one study, the response to HIV gag was polyisotypic (all/most class or subclasses, IgM, IgG1, IgG3 and IgA) but antibodies to env were strikingly restricted to IgG1, (Khalife et al 1988, AIDS Res. and Hu. Retroviruses 4:3). The immune response to the nonstructural protein F (3' orf) also was restricted to IgM, IgA and IgG1 but not as much as the response to env and Khalife, et al, ibid further noted that IgG4 and IgE response which was gag restricted was also restricted to Hemophiliacs group.

Interestingly, in regard to man and HIV it is recognized that the disappearance of a particular subclass of antibodies IgG3 to a conserved p17 protein molecule is most closely associated with disease progression. Antibodies to HIV of IgG1 and IgG2 subclasses are found in nearly all sera from HIV infected individuals at different stages of the disease. However, the presence of IgG3 is largely associated with gag proteins (p17, p24 and p55). conversely almost all antibodies to the major viral surface proteins p41 and gp120 are of the IgG1 subclass and are present even in late stage disease (McDougal et al 1987 J. Clin, Invest 80:316–24).

The findings of McDougal et al ibid and also Jiang et al (J AIDS 1992, 5:382) are, in part, at odds with those of Broliden et al (1989 Clin. Expt. Immunol. 76: 216). Broliden ibid found IgG3 antibodies, predominantly against gag proteins at all stages of disease, and IgG1 which was against all HIV antigens declining in latter stages of the disease in contrast to McDougal et al ibid. Jiang et al ibid showed that anti p17 antibodies declined with disease progression and, in part, this was associated with antibodies to certain peptides of p17 including HGP-30. Broliden et al, ibid, refer to neutralizing antibody as being of the IgG3 subclass but conclude that no HIV neutralizing antibodies of IgG3 have been found. Broliden et al, ibid, in their study relates with HIV ADCC to IgG1 and not IgG3, (see also Ljunggren et al 1987,8, J. Immunol Meth 104:7, Clin Exp. Immunol 1987, 73:343). Others suggest that ADCC is associated with IgG3. Often it is found that ADCC is associated with IgG3 ("The Human IgG Subclasses: Molecular Analysis of Structure, function and Regulation" Shakib, F. ed., Pergamon Press, 1990: Jeffries et al, Chapter 6, p.93; Pound et al, Chapter 7, p.111; Weiner, Chapter 8, p.135).

Rook et al (J. Immunol 1987, 138:1064) have shown that ADCC was associated with higher levels of antibodies to gag p24 than env. These workers did not examine antibodies to p17, various synthetic peptides of the proteins or the isotypes of the antibodies. Rook et al, ibid, also demonstrated higher levels of ADCC in asymptomatic HIV seropositive individuals than in AIDS patients.

The SCID Hu PBL mouse provides a very useful model that can be reconstituted with human cells and that can be infected with multiple strains of HIV (Mosier et al 1991, Science 251:791). This model allows for studying not only infection but also immunological intervention and control. Use of recombinant (r) gp160 (rgp160) for vaccination and demonstration of limited and short lived protection in the SCID model has been shown by Mosier et al (1993, Proc. Nat Acad. Sci 90:2443–2447). They showed the usefulness of this model in a preliminary report (Mosier et al, 1992, AIDS Res. Hu. Retroviruses 8:1387). Anti HIV neutralizing antibody has been shown by passive immunization in this SCID hu model to afford some protection (Parren et al 1995, AIDS 9(6):Fl-6).

An interesting finding for p17, one of the two major gag proteins, involved a region thereof of 30 amino acids, namely the peptide HGP-30, whose sequence contains T and B cell epitopes immunoreactive with p17 of HIV (Sarin et al 1986, Science 232:1135;

Naylor et al 1987, Proc Nat. Acad Sci 84:2951–5). See also U.S. Pat. No. 4,983,387 to Goldstein, et al, the entire disclosure of which is incorporated herein by reference thereto. This peptide has been conjugated to a large protein, Keyhole Limpet Haemocyanin (KLH), and found to be immunogenic in various animals and man, and the conjugate is well tolerated in both animals and humans (Gazzard, et al.; 1992, Vaccine Res. 1:129; Sarin, et al, 1994, Vaccine Res. 3: 495; Kahn 1992, AIDS Res Hu Retroviruses 8:1321; Naylor et al 1991, Int J. Immunopharm 13(Suppl):117). A pilot study of HGP-30 vaccine has shown protection from HIV infection in such SCID hu mice given PBL from HGP-30 immunized donors (Sarin et al 1995, Cell Molec Biol 41:401). More recently it has been shown that the presence of a predominance of IgG3 antibodies in serum of HGP-30 vaccine immunized human donors correlates with protection by PBL in the SCID Hu mouse HIV virus challenge model (Kahn et al 1996, Abstract 13 International AIDS Conference, Vancouver, Canada, July 1996; Talmadge et al 1996, Clin Immunol, Meeting New Orleans LA June 1996).

Traditionally, small peptides must be attached to carrier proteins in order to elicit immune responses. Often a large protein such as KLH is used.

With the recent recognition of the need to specifically direct the immune response various methods are under investigation. Use of protein carriers to direct nature of the immune response such as antibody, TH1, TH2, TS subclass of antibodies and CTL is now being characterized. Conjugation of HIV to Brucella abortus has been used to stimulate IgG2a in mice with the goal of stimulating IgG3 in humans, as shown by the following quote from the authors:

> " . . . From a functional point of view, IgG3 is the human counterpart of murine IgG2a . . . ."

Golding et al 1991, AIDS Res HU Retroviruses 7:435. This is based upon the evidence part of which was previously cited, namely, Pound et al, ibid, Weiner et al, ibid, Jeffries et al, ibid.

Considering the correlation of human IgG3 to murine IgG2a suggested by Golding et al, 1991, ibid the following statements can be made. Protein antigens induce IgG1, IgG3 and IgG4 in man and IgG1 and IgG2 in mice (Shakib, 1990, ibid, at Chap. 15, p. 301, Hammarstrom et al). Allergens induce IgG4 and IgE in man (and IgG1 and IgE in mice (Shakib, 1990, ibid, at Chap. 13, p. 251, Snapper). Carbohydrates induce Ig3 in mice and IgG2 in man (Hammarstrom et al ibid). ADCC is associated with IgG1 and IgG3 in man and IgG2 in mice (Shakib, 1990, ibid, at Chap. 13, p. 111, Pound, et al.). Complement binding activities are associated with IgG1 and IgG3 for man and IgG2a and IgG2b in mice (Hammarstom et al ibid; Pound et al, ibid). TH1 cytokines such as interferon γ inhibit IgG1 in man (Kawano et al 1994, J. Immunol. 153:4948) and IgG1, IgG2a and IgE in mice, (Snapper, ibid). IL-4 and IL-5 which stimulate TH2 responses stimulate IgG1 and IgE in mice, and IgG1 and E in man (Lundgren et al 1989, Eur J Immunol 19:1311; Snapper et al, ibid).

Since in man KLH induces IgG1 and IgG2 in early stages and also IgG4 after prolonged immunization (Bird et al, 1990, Immunol. 69:355) it is desirable to find other methods to direct the response to IgG3, a TH1 associated pathway, since there is a need for a directed response with IgG3 as a marker (McDougal et al ibid, Kahn et al, 1996, ibid).

The use of adjuvants to direct immune response to a cellular or humoral pathway has shown that in the mouse alum directs the system more toward IgG1 production and a poor DTH response, whereas Freund's complete adjuvant induces stronger DTH and IgG2a responses (Hadjipetrou-Kourounakis et al 1984, Scan J. Immunol 19:219; Kenney et al 1989, J. Immunol. Meth 121:157–66; van de Wihgert et al 1991, Infect Immun 59:2750; Golding et al 1994, ibid). The route of administration for TH1 or TH2 directed by adjuvants from Syntex SAF-1 and RIBI has also been reported (Golding et al 1994, Am J. Trop. Med Hyg. 50(4) suppl):33). Likewise, the use of cytokines in vaccine formulations has also been evaluated and although showing promising results have been obtained such use of cytokines in vaccines has limited value (Lachman et al 1995, AIDS Res Hu Retroviruses 11(8):921; Bui et al 1994, J. AIDS 7:799).

There is no evidence that changing the nature of a peptide, such as addition or deletions of several amino acids and/or method of attachment to a carrier could or would influence the subclass of antibody generated that recognize the epitope, even though it is known that such manipulations can induce different responses such as the stimulation of B and T cells, cytotoxic and lymphoproliferation responses. However, the effect of T cell epitopes on antibody responses that has been reported have been for the presence or absence of antibody by helper (TH) or suppressor (TS) immune responses (Sercarz et al 1991, Immunol Today 12:111; Yowell et al 1979 Nature 279:70; Wicker et al 1984, Eur J. Immunol. 14:442).

Zimmerman et al (1996a,b, Vaccine Res 5:91; 5:103; WO 89/12548) have taught that addition of a TCBL to a peptide epitope could alter the nature of the immune response (i.e., TH1 or TH2). These authors further showed that the antibodies induced by such heteroconjugates were better able to recognize the native molecule than were the antibodies induced by using a peptide-KLH conjugate.

SUMMARY OF THE INVENTION

Prior work has established that p17 can be subdivided into several peptides for induction of immune responses (Goldstein et al U.S. Pat. No. 4,983,387; EP 0 246 829 Sarin, et al; Jiang et al 1992, J. AIDS 5:382). That and other work has shown that in the p17 molecule numerous immunological epitopes are present for activities such as B cell epitopes for induction of antibody, T cell epitopes for helper activity and generation of cytotoxic T cells (Naylor et al 1990, Mono. Viro 18:74; Coates et al, 1987, Nature 326:549; Wahren et al 1989, J AIDS 4:448; Broliden et al, ibid, Clin Exp Immunol 76:216; Papsidero et al, 1989, J. Virol 63:267 ; Boucher et al, 1990, Clin Lab Anal 4:43). Other work has shown that certain conjugates which include a T cell binding ligand (TCBL) and an epitope of interest from a disease associated antigen can also have biological activity even where the epitope alone is inactive (Zimmerman et al, 1996a,b ibid).

The present invention, relates to peptide fragments of the p17 gag protein of HIV containing epitopes in and/or near to one specific peptide of p17 called HGP-30 which has the following sequence:

```
Y S V H Q R I D V K D T K E A    (SEQ ID NO:1)
L E K I E E Q N K S K K K A
```

More particularly, the invention relates to antigenic peptides of p17 which include at least the first through at least the 22nd amino acids of HGP-30 and, preferably, the first to 26th or 27th amino acids of HGP-30 and extending from the first amino acid (i.e., N-terminal) for at least three and up to about 10 contiguous amino acids at the C-terminal end of the specific adjacent peptide of p17 called HGP-35; and to such peptides conjugated to an immunogenic carrier; as well as to the use of such peptide-carrier constructs for eliciting immunization to infection against Human Immunodeficiency Virus, HIV, in a human subject.

More particularly, the antigenic peptide of this invention is capable of eliciting TH1 associated antibodies when administered to a human in need thereof and has an amino acid sequence having sequence homology extending from between amino acid at position 75 to position 82 and extending to between amino acid at position 106 to position 111 of p17 gag protein of HIV, for a total of between about 25 and 37 amino acids.

The invention also provides an immunologically active peptide comprising a peptide-carrier construct having the formula (I):

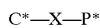  (I)

wherein

C* represents an immunogenic carrier material;

P* represents a peptide according to claim 1; and

X represents a direct bond or covalent linkage linking the immunogenic carrier material C* and the peptide P*.

In another aspect, the invention provides a composition effective for eliciting a TH1 immune response when administered to a human patient in need thereof comprising an immunologically active peptide of the formula C*—X—P* as set forth and an immune response adjuvant.

There is also provided a method for eliciting at least a TH1 response in a human patient in need thereof comprising administering to said patient an immunologically effective amount of an immunologically active peptide of the formula C*—X—P* as set forth above. The method preferably further comprises administering the immunologically active peptide in combination with an immune response adjuvant.

DETAILED DESCRIPTION OF THE INVENTION AND PREFERRED EMBODIMENTS

For the peptides disclosed above and below and as employed in the experimentation described herein the amino acid sequences thereof, are set forth by the single identification letter symbol as follows:

| Amino Acid | Three-letter abbreviation | One-letter symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

In addition to recent discoveries leading to the conclusion that HIV p17 is located near the surface of the HIV virion rather than in the internal core as in the case of p24 gag protein, it has been shown that the p17 gag protein is myristylated at its N-terminal; see, e.g., the EP 0 245 829, incorporated herein by reference thereto. Furthermore, analysis of the peptide (designated HGP-30, SEQ ID NO:1), which is located nearer to the C-terminal of p17, suggests that this peptide contains an immunodominant B-cell epitope which could induce antibodies that mediate cytotoxicity through the ADCC type mechanisms. On the other hand, the peptide designated HGP-35 at amino acid positions 51–84, has an amino acid sequence consistent with a T-cell epitope, therefore capable of eliciting a T-cell immunological response. Analysis of the intermediate region peptide of p17 at positions 33–50 (also designated HGP-18), near the N-terminal suggests that this peptide has the appropriate balance of hydrophilicity and hydrophobicity to constitute a transmembrane region peptide if the appropriate charge neutralizing membrane proteins are present.

It is well known that HGP-30 having SEQ ID NO:1 contains regions with well defined B cell epitopes and other regions with defined T cell epitopes (defined as epitopes stimulating lymphoproliferation responses and others that stimulate cytotoxic T cells) (Jiang et al ibid). While not studied in the HGP-30 sequence it is well known that other T cell epitopes include ones which are suppressive in other systems (Wicker et al, 1984, Eur. J. Immunol. 14:442). The B cell epitopes are based upon stimulating the production of antibodies, presumably IgG1 in mice, or of being recognized by antibodies in seropositive individuals. No discrimination as to subclasses in man is made. It was reasoned that if IgG3 in man or IgG2a in mice were the desired type of antibodies and an indicator of the arm of the immune response being stimulated (TH1 or TH) then to include several residues from the T cell epitope region at the amino terminus may be of benefit along with deletion of several residues at the carboxyl terminus at the B cell epitope region. Therefore, a modified HGP-30 peptide sequence was studied. It was reasoned that T cell epitopes such as cytotoxic cell epitopes might not be suppressive but could direct the immune response toward a TH1 type response. That being the case the inventors postulated that TH1 correlates with cellular mechanisms of immune responses, the TH1 effect includes not cytotoxic cells but antibody dependent cellular cytotoxicity (ADCC) and complement binding antibodies, both of which are properties of IgG2a in the mouse and IgG3 in man. Therefore, the antibody response induced is towards IgG2a. For more details on HGP-30 and the immune response to the various epitopes see, e.g., Gazzard et al 1992, Vaccine Res. 1:129; Sarin et al 1994, Vaccine Res. 3:49; Willer et al 1992 Biomed. & Pharmacol. 46:359; Naylor et al 1991, Int. J. Immunopharm. 13(Suppl 1):117; Jiang et al 1992, AIDS Res. 5:382; also U.S. Pat. No. 4,983,387; the disclosures of these documents are incorporated herein in their entireties by reference thereto).

In particular, the peptides useful in this invention will generally be between about 25 and 37 amino acids and may extend between consecutive amino acids beginning at between about position 75 to position 82 and extending to between about position 106 and position 111 of p17 gag protein of HIV, as represented in the following representative cases:

```
A T L  Y S V  H Q R  I D V  K D T    (SEQ ID NO:2)
K E A  L E K  I E E  E

S L Y  N T V  A T L  Y S V  H Q R    (SEQ ID NO:3)
I D V  K D T  K E A  L E K  I E E
E Q N  K S K

R S L  Y N T  V A T  L Y S  V H Q    (SEQ ID NO:4)
R I D  V K D  T K E  A L E  K I E
E E Q  N K S  K
```

A particularly preferred peptide for use in this invention has the following amino acid sequence

```
A T L  Y S V  H Q R  I D V  K D T    (SEQ ID NO:5)
K E A  L E K  I E E  E Q N  K S
``` hereinafter referred to, for convenience, as m-HGP-30, representing a modified version of HGP-30. More generally, however, all of the peptides for use in the present invention may, for convenience, be referred to generically as "modified HGP-30."

It should be understood that in any of the above amino acid sequences variations of specific amino acids, such as conservative amino acid substitutions, which do not adversely effect the desired biological activity are contemplated and fall within the scope of the invention. In particular, it is recognized that the foregoing sequences are based upon a specific variant or species of HIV, namely, HIV-1SF2, (from Consensus B) and, although this p17 gag region of HIV is fairly highly conserved, other naturally occurring and spontaneously occurring variants, within Consensus B, or any of the other consensus regions, and which include one or several variations of the amino acids, are also within the scope of the antigenic peptides of this invention. Such natural and spontaneously occurring amino acid variations are specifically contemplated for use in this invention and, in certain cases, it may be advantageous to use mixtures of peptides, the sequences of which fall within the guidelines given above, and are discussed in more detail below, corresponding to two or more natural and spontaneously occurring variants of HIV. Still further, as well recognized in the art it is often advantageous to make specific amino acid substitutions in order, for example, to provide specific binding sites or for purpose of radioactive or fluorescent tagging of the peptide. Such "designed" amino acid sequences are also within the scope of the antigenic peptides (i.e., modified HGP-30) of this invention.

Examples of different consensus sequences of HIV which are also specifically included within the scope of the modified HGP-30 antigenic peptides for use in the heterofunctional conjugates of this invention include, for instance, the following, wherein the lower case letters represent cites of amino acid variability resulting from the allelic variations, genetic drift and mutations of the particular consensus sequence; the presence of a "?" symbol reflects that there is no agreed upon consensus for the amino acid at that position of the consensus sequence:

CONSENSUS A:

```
kSL fNt vat LyC vHq rId        SEQ ID NO:6
vkD tKe Ald kiE eiq nks k
```

CONSENSUS B:

```
rSL yNt vat Lyc VHq rIe        SEQ ID NO:7
VkD tKe Ald kiE eEq nks k
```

CONSENSUS C:

```
rSL ?Nt vat LyC vH? ?Ie        SEQ ID NO:8
vrD tKe Ald kie eEq nk? Q
```

CONSENSUS D:

```
kSL ?Nt vat LYc VHe rIe        SEQ ID NO:9
vkd tKe Ale kmE eEq nks k
```

CONSENSUS F:

```
rSL ?Nt v?v Lyf vHq rvE        SEQ ID NO:10
?kD tke Ale EVE Kaq kQq k
```

CONSENSUS G:

```
kSL ?N? ?a? L?C ?Hq rI?        SEQ ID NO:11
vkD tke Ale EVE Kaq kns k
```

CONSENSUS H:

```
QSL fNl la? LyC vHq rId        SEQ ID NO:12
?kD tKe Al? k?? eqn ?Q? ?
```

CONSENSUS O:

```
?SL WNA I?V LWC vHN r??        SEQ ID NO:13
I?D tQQ AIQ kLK eVM ?kS A
```

In the following representative species of the various consensus sequences the amino acids corresponding to positions 94 to 111 have not been set forth, however, these may be readily ascertained by reference to the published sequences of the various strains of HIV.

For example, for Consensus sequence A above the following species have been identified; the dashes represent identity of amino acid with the consensus sequence:

```
CONSENSUS.A  rSL fNt vat LyC VHq rId vk  SEQ ID NO:6

HIV-1U455    R-- Y-T VAV -Y- --Q R-D VK  SEQ ID NO:14

HIV-1MAL     K-- Y-T VAG -Y- --Q R-D VK  SEQ ID NO:15

HIV-1TN243   K-- F-T VAT -W- --Q R-E VK  SEQ ID NO:16
```

The following are examples of Consensus Sequence B above:

```
CONSENSUS.B  rSL yNt vAt LYC vHQ rIe vk  SEQ ID NO:7

HIV-1SF2     R-- Y-T V-T --- V-- R-D VK  SEQ ID NO:17

HIV-1TB132   R-- Y-T I-V --- V-- K-E VK  SEQ ID NO:18
```

```
                -continued
HIV-1LAI    R-- Y-T V-T --- V-- R-E IK SEQ ID NO:19

HIV-1HXB2R  R-- Y-T V-T --- V-- R-E IK SEQ ID NO:20

HIV-1MN     K-- Y-T V-T --- V-- K-E IK SEQ ID NO:21

HIV-1JH3    K-- F-T V-T --- V-- R-E VK SEQ ID NO:22

HIV-1JRCSF  T-- Y-T V-T --- V-- R-E IK SEQ ID NO:23

HIV-1OYI    R-- Y-T V-T --- V-- K-E VK SEQ ID NO:24

HIV-1NY5CG  R-- F-T V-V --- V-- R-D VK SEQ ID NO:25

HIV-1NL43   R-- Y-T I-V --- V-- R-D VK SEQ ID NO:26

HIV-1CDC4   R-- Y-T V-T --- V-- R-E VR SEQ ID NO:27

HIV-1HAN    R-- Y-T V-T --- V-- K-E VK SEQ ID NO:28

HIV-1CAM1   R-- Y-T V-T --- V-- K-D KV SEQ ID NO:29

HIV-1RF     K-- Y-A V-T --- V-- N-E VR SEQ ID NO:30

00HIV-1D31  R-- F-T V-T --- V-- R-E IK SEQ ID NO:31

HIV-1BH102  R-- Y-T V-T --- V-- R-E IK SEQ ID NO:32

HIV-1PV22   R-- Y-T V-T --- V-- R-E IK SEQ ID NO:33

HIV-1JRFL   R-- Y-T V-T --- V-- R-E VK SEQ ID NO:34
```

The following are exemplary of the sequences for species of Consensus Sequence C:

```
CONSENSUS.C rSL ?Nt vat Lyc VH? ?ie vr SEQ ID NO:8

HIV-1ZAM18  K-- F-T VVT -WC --E DIT VR SEQ ID NO:35

HIV-1ZAM19  K-- H-A VAV -YC --K XIT VR SEQ ID NO:36

HIV-1ZAM20  R-- Y-T VAT -YC --A GIE VR SEQ ID NO:37
```

Consensus Sequence D includes the following exemplary species:

```
CONSENSUS.D kSL yNT VAT LYC VH? RiE VK SEQ ID NO:9

HIV-1ELI    R-- Y-- --- --- --K G-D -K SEQ ID NO:38

HIV-1ZUZ6   R-- F-- --- --- --E R-E -K SEQ ID NO:39
```

```
                -continued
HIV-1NDK    R-- Y-- --- --- --E R-E -K SEQ ID NO:40
```

Similarly, other naturally occuring species within Consensus A, Consensus B, Consensus C, Consensus D, as well as Consensus F, Consensus G, Consensus H, Consensus O, whether presently known or existing, or subsequently discovered or subsequently arising, can be used as the modified HGP-30 antigenic peptide of this invention. It is well known in the art that these various consensus sequences are generally derived from, and are prevalent in different geographical regions of the world and are often referred to as "clades" (also known as "subtypes") of the HIV virus. Representative of these clades of modified HGP-30 include the following consensus sequences (wherein the letter designations generally correspond to the consensus sequences as given above) and any allelic variations thereof (in the following sequences the amino acids at positions corresponding to position numbers 85 to 114 are shown; the amino acid at positions 74 to 84, for example, corresponding to the C-terminal end residues from fragment HGP-35 of p17 gag protein, may be obtained from any of the available published sequences of HIV):

```
Thailand-B:   YCV HQK IEV KDT KEA LEK IEE EQN KSK KKA SEQ ID NO:41

Thailand-A/E: WCV HQR IEV KDT KEA LDK IEE VQN KSQ QKT SEQ ID NO:42

Uganda-A:     YCV HQR IDV KDT KEA LNK IEE MQN KNK QRT SEQ ID NO:43

Kenya-A:      YCV HQR IDV KDT KEA LDK IEE IQN KSK QKT SEQ ID NO:44

Brazil-A/E:   YFV HQR VEV KDT KEA LDK LEE EQN KSQ QKT SEQ ID NO:45

Brazil-B:     YCV HQK IDV RDT KEA LEK VEE EQN KSK EKA SEQ ID NO:46

Uganda-B:     YCV HQR IDV KDT KEA LDK IEE EQN KSK KKE SEQ ID NO:47

Uganda-C:     YCV HKG IEV RDT KEA LDK IEE EQN KIQ QKT SEQ ID NO:48

India-C:      YCV H?? IEV RDT KEA LDK IEE EQN K?Q QKT SEQ ID NO:49

Uganda-D:     YCV HER IKV ADT KEA LDK IEE EQT KSK KKA SEQ ID NO:50
```

As can be seen from the above aligned consensus sequences and species for the various consensus sequences, there is some variation amongst HIV subtypes in the gag protein sequence. Moreover, there is considerable variation in the specific numbering of amino acids among different HIV strains. In the present invention, the numbering of sequences is based on the sequence of HIV strain 1SF2 or MN; however, it is the amino acid sequence itself, allowing for variations observed amongst HIV subtypes, that is important. The sequences listed above are illustrative of the types of amino acid changes that can be made in the antigenic modified HGP-30 peptides of the invention and the conjugates based thereon. In addition to the variations in the amino acids among the various HIV strains, it is also recognized that the amino acids at the N-terminal and C-terminal may be present as the free acid (amino or carboxyl groups) or as the salts, esters, ethers, or amides thereof. In particular amide end groups at the C-terminal and acetylation, e.g., myristyl, etc. at the N- or C-terminal, are often useful without effecting the immunological properties of the peptide.

The peptides of the present invention can be prepared by conventional processes for synthesizing proteins, such as, for example, solid phase peptide synthesis, as described by Merrifield, R. B., 1963, J. of Am. Chem. Soc., 85:2149–2154, incorporated herein by reference thereto. It is also within the scope of the invention and within the skill in the art to produce the novel peptides of this invention by genetic engineering technology.

In the present invention, any of the modified HGP-30 antigenic peptides may be used coupled to an immunogenic carrier material to produce an antigenic peptide-carrier construct. Generally, natural and synthetic proteins having a high molecular weight which are conventionally employed in the preparation of antigens can be employed as the immunogenic carrier material. In addition, however, smaller peptides or molecules, such as tuftsin (a tetrapeptide), analogs of tuftsin, and muramyl dipeptides, and its analogs, can also be used as "immunogenic carrier materials."

As used herein the term "immunogenic carrier material" is meant to include those materials which have the property of independently eliciting an immunogenic response in a host animal and which can be covalently coupled to peptide either directly via a formation of peptide or ester bonds between free carboxyl, amino or hydroxyl groups in the polypeptide and corresponding groups on the immunogenic carrier material or alternatively by bonding through a conventional bifunctional linking group. Examples of such carriers include albumins of animal sera such as horse serum albumin, bovine serum albumin, rabbit serum albumin, human serum albumin, sheep serum albumin, etc.; globulins of animal sera such as horse serum globulin, bovine serum globulin, rabbit serum globulin, human serum globulin, sheep serum globulin, etc.; thyroglobulins of animals such as horse thyroglobulin, human thyroglobulin, sheep thyroglobulin, etc.; hemoglobulins of animals such as horse hemoglobulin, bovine hemoglobulin, rabbit hemoglobulin, human hemoglobulin, sheep hemoglobulin, etc.; hemocyanins of animals such a Keyhole limpet hemocyanin (KLH), etc.; proteins extracted from ascaris (ascaris extracts, such as those described in Japanese Patent Application (OPI) No. 16,414/81, *J. Immun.*, 111, 260–268 (1973), ibid., 122, 302–308 (1979), ibid. 98, 893–900 (1967) and *Am. J. Physiol.*, 199, 575–578 (1960), or purified products thereof); polylysine, polyglutamic acid, lysine-glutamic acid copolymers, copolymers containing lysine or ornithine, etc. Recently, vaccines have been produced using diphtheria toxoid or tetanus toxoid as immunogenic carrier materials (see Lepow, M. L., et al., *J. of Infectious Diseases*, Vol. 150, No. 3, page 402–406 (1984); and Coen Beuvery, E., et al. *Infection and Immunity* 40, pages 39–45 (April 1983) and these toxoid materials can also be used herein. Other suitable carriers are disclosed in, for example, U.S. Pat. No. 4,575, 495, including vaccines, organic polymers, etc.

As hapten-carrier linking agents, those conventionally employed in the preparation of antigens can be widely employed. Specific examples of these agents include diazonium compounds for crosslinking tyrosine, histidine, tryptophane, etc., e.g. bisdiazotized benzidine (BDB), etc.; aliphatic dialdehydes for crosslinking an amino group with an amino group, e.g. $C_2$–$C_7$ alkanals, such as glyoxal, malonedialdehyde, glutaraldehyde, succinaldehyde, adipaldehyde, etc.; dimaleimide compounds for crosslinking a thio group with a thio group, e.g. N,N'-o-phenylenedimaleimide, N,N'-m-phenylenedimaleimide etc.; maleimidocarboxyl-N-hydroxysuccinimide ester for crosslinking an amino group with a thiol group, e.g. metamaleimidobenzoyl-N-hydroxysuccinimide ester, 4-(maleimidomethyl)-cyclohexane-1-carboxyl-N'-hydroxysuccinimide ester, etc.; agents used in conventional peptide bond forming reactions in which amide bonds are formed from an amino group and a carboxyl group, e.g. dehydrating and condensing agents such as carbodiimides, e.g. N,N-dicyclohexylcarbodiimide, N-ethyl-N'-dimethylaminocarbodiimide, 1-ethyl-3-diisopropylaminocarbodiimide, 1-cyclohexyl-3-(2-morpholinyl-4-ethyl)carbodiimide, etc. As the foregoing hapten-carrier linking agent, it is also possible to use diazonium aryl carboxylic acids such as p-diazonium phenylacetic acid, etc., with conventional peptide bond forming agents such as the dehydrating and condensing agents described above in combination.

The covalent coupling of the invention peptide or analog thereof to the immunogenic carrier material can be carried out in a manner well known in the art. Thus, for example, for direct covalent coupling it is possible to utilize a carbodiimide, most preferably dicycloheylcarbodiimide or 1-ethyl-3-(3-dimethylaminopropyl)carbondiimide as coupling agent. In such direct coupling it is desirable to utilize a slightly acidic reaction medium for this step, e.g. a medium having a pH in the range of from about 3 to 6.5, most preferably in the range of from about 4 to 6.5.

The coupling reaction for preparing antigens using as haptenes those peptides that are neutral or alkaline can be carried out in similar manner but in an aqueous solution or conventional buffer solution having pH of 7 to 10, preferably in a buffer solution having pH of 8 to 9, at temperatures of about 0° to 40° C., preferably around room temperature. The reaction is generally completed within about 1 to about 24 hours, preferably 13 to 5 hours. Representative examples of buffer solutions which can be used in the above process include:

0.2 sodium hydroxide-0.2M boric acid 0.2M potassium chloride buffer solution;

0.2M sodium carbonate-0.2M boric acid 0.2M potassium chloride buffer solution;

0.05M solution tetraborate-0.2M boric acid 0.2M sodium chloride buffer solution;

0.1M dihydrogen potassium phosphate 0.05M sodium tetraborate buffer solution.

In the above, proportions of the hapten, hapten-carrier linking agent and carrier can be appropriately determined but it is preferred that the carrier be employed in an amount of about 1 to about 6 times, preferably about 1 to about 5 times the weight of the hapten and the hapten-carrier linking agent be employed in an amount of about 5 to about 10 times the mol of the hapten. By the above reaction, the carrier is bound to the hapten via the hapten-carrier linking agent to obtain a desired antigen composed of a peptide-carrier complex.

After completion of the reaction, the thus obtained antigen can easily be isolated and purified by means of a dialysis method, a gel filtration method, a fractionation precipitation method, etc.

The thus obtained antigen binds 5 to 60 mols on average of the peptide thereto per mole of a protein and enables one to subsequently prepare an antibody having a high specificity to the antigen. Particularly, antigens to which the peptide is bound in an amount of 5 to 20 mols, preferably 8 to 15 mols, in average, per mol of a protein are preferred since they have higher specificity and enable one to obtain antibodies having high activity and sensitivity.

The peptide-carrier constructs according to the invention may be broadly represented by the formula (I):

$$C^*\text{---}X\text{---}P^* \qquad (I)$$

where

C* represents an immunogenic carrier material, as defined above;

P* represents a modified HGP-30 peptide; and

X represents a direct bond or covalent linkage linking the immunogenic carrier C* and modified HGP-30 peptide P*.

Any of the known methods for forming peptide constructs can be used in this invention. For instance, using a method adapted from Ziegers, et al, 1990, J. Immunol. Meth., 130:195–200, the antigenic modified HGP-30 peptide is coupled to KLH or other suitable immunogenic carrier material by activating the KLH by dialysis against 0.2% glutaraldehyde in PBS for 16 hours at 4° C. followed by dialysis against PBS (3 times, 500 ml each). The peptide is added to the activated KLH (100:1 molar ratio) and the mixture is stirred at 4° C. for 16 hours. Lysine is added to a final concentration of 20 mM to block the unreacted activated KLH and stirred for 2 hours at 4° C. Excess peptide and lysine are dialyzed against PBS (2 times; 200 ml ea) at 4° C.

The invention also concerns a method for treating or preventing Acquired Immunodeficiency Complex (AIDS) by administering to a human patient in need thereof a therapeutically effective amount of the peptide-carrier construct of formula (I).

According to this invention the immune response to modified HGP-30 of p17 molecule from HIV can be directed toward at least the desired TH1 as evidenced by the examples of the TH1 characteristic antibody IgG2a (mouse) and presumably thereby IgG3 (man). These peptides may, however, in addition to the TH1 elicited immune response, elicit a TH2 immune response, and in particular, a mixed TH1/TH2 immune response.

Accordingly, the antigenic peptides of this invention provide potentially powerful vaccines for preventing infection by, or treating cells infected by, HIV. Therefore, the present invention provides such vaccine compositions which can be used to immunize patients at risk for AIDS, or exposed to HIV, particularly HIV-1, as well as treating patients with AIDS-related Complex or with frank AIDS.

The present invention, therefore, provides antigenic p17 gag protein peptides, which provide powerful vaccines for neutralizing HIV-1 and killing HIV-1 infected cells. Therefore, the vaccines of this invention can be used to immunize patients at risk for AIDS, or exposed to HIV-1 or to treat patients with AIDS-Related Complex or with frank AIDS.

When used as a vaccine in the method of this invention, the vaccine can be introduced into the host most conveniently by injection, intramuscularly, intradermally, parenterally, orally or subcutaneously. Any of the common liquid or solid vehicles may be employed, which are acceptable to the host and which do not have any adverse side effects on the host or any detrimental effects on the vaccine. Phosphate buffered saline (PBS), at physiological pH, e.g. pH 6.8 to 7.2, preferably pH 7, may be used as a carrier, alone or with a suitable adjuvant. The concentration of immunogenic antigen may vary from about 10 to 200 μg/kg, such as about 50 μg/kg per injection, in a volume of solvent generally from about 0.25 to 1 ml, such as about 0.5 ml. Multiple injections may be required after the initial injections and may be given at intervals of from about 2 to 4 weeks, for example, about 2 weeks, when multiple injections are given.

Cytotoxic T-cell responses have been observed in human volunteers immunized with CTL epitope containing peptides, however, CTL response appears to be dependent, in part, at least, upon the concentration of immunogenic antigen in the vaccine. A higher proportion of gag peptide vaccinees who received a dose of from 10 to 25 μg/kg showed CTL responses than vaccinees who received a higher does of from 50 to 100 μg/kg (Sarin, et al., 1995, *Cell. Mol. Biol.* 41:401–407). These results suggest that TH-1 type cells, which have been implicated in cell mediated immunity (Clerici, et al., (1993), *Immuno. Today* 14:107–111), are induced at lower doses of CTL containing peptide vaccine. The lower proportion of CTL response among vaccinees immunized with a higher dose of peptide suggest that higher vaccine doses predominantly induce TH-2 type cells involved in humoral immun response. Accordingly, the preferred concentration of immunogenic antigen in the vaccines of the present invention is in the range of from 10 to 25 μg/kg, however, a higher dose may be administered as needed.

The following are exemplary of applications for various embodiments of the antigenic peptides and constructs and compositions of this invention; but, it is understood that the invention is not restricted to, the following described examples.

Embodiment 1: Use of KLH conjugate as a carrier for the modified HGP-30 sequence to direct the immune response as a prophylactic vaccine for a TH1 directed immune response to prevent HIV infection.

Embodiment 2: Use of KLH conjugate as a carrier for the modified HGP-30 sequence to direct the immune response as a therapeutic vaccine for a TH1 directed immune response in HIV infected persons which may be used in conjunction with other therapies to reduce viral load and control or cure HIV infection.

Embodiment 3: Use of Human IgG, Bovine or Human serum albumin or other carrier proteins for use in the conjugate as a carrier for the modified HGP-30 sequence to direct the immune response as a prophylactic vaccine for a TH1 directed immune response to prevent HIV infection.

Embodiment 4: Use of Human IgG, Bovine or Human serum albumin or other carrier proteins for use in the conjugate as a carrier for the modified HGP-30 sequence to direct the immune response as a therapeutic vaccine for a TH1 directed immune response in HIV infected persons alone or in conjunction with other therapies to reduce viral load and control or cure HIV infection.

In particular, in the following examples the modified HGP-30 peptide that was used was that of m-HGP-30 (SEQ ID NO:5) as follows:

```
A T L    Y S V  H Q R  I D V  K D T   (SEQ ID NO:5)
K E A    L E K  I E E  E Q N  K S
```

The peptides were all synthesized by Quality Controlled Biochemicals, Inc. (QCB) (Hopkinton, Mass.) using the FMOC procedure and a double coupling protocol for the first 8 residues. Usually, the peptide is prepared with the carboxyl terminus as an amide form. All of the peptides were purified at QCB using preparative HPLC, and analyzed by an analytical HPLC, amino acid analysis and mass spectrophotometer. The peptides were greater than 95%, usually greater than 98%, pure by HPLC criteria. The dry peptides obtained from QCB were stored in glass vials with desiccant at −20° C.

II. Preparation of Conjugates (Peptide-Carrier Constructs)
KLH Conjugations

Keyhole Limpet Haemocyanin (KLH) (Pierce) was conjugated to the HGP-30 peptide of SEQ ID NO:1 or the m-HGP-30 (SEQ ID NO:5) by a glutaraldehyde conjugation method (Naylor et al 1987, Proc. Nat. Acad. Sci. 84:2951; incorporated herein by reference thereto. KLH was also conjugated to HGP-30 and m-HGP-30 via 1-ethyl-3-(dimethyl aminopropyl)carbodiimide (EDC) (Williams et al, 1981, J.Amer. Chem. Soc. 103:7090; Gilles et al, 1990. Anal. Biochem. 184:244). This allows to evaluate if the method of conjugation was important as far as the nature of the immune response evoked. In both cases a 1:1 mg weight ratio of peptide to KLH was used. Conjugation of the HGP-30 peptide and the m-HGP-30 peptide to KLH was also carried out by formation of a thioether using a halogenated N-terminal acetyl derivative (Linder et al, Int. J. Peptide Chemistry, 30:794 (1987); Robey et al Anal. Biochem. 177:373 (1989); Kolodny et al Anal. Biochem. 187:136 (1990 and Robey et al U.S. Pat. No. 5,066,716; the disclosures of which are incorporated herein by reference thereto). To reduce any oxidized sulfhydryls or disulfides that may have formed during storage, there was added to the KLH, an equal volume of tris-(2-carboxylethyl)phosphine (TCEP) (5.0 mg/ml in 0.2 M sodium phosphate buffer, pH 6.8) (Pierce, Rockford, Ill.). Next, 50 $\mu$l of 0.1 M ethylenediaminetetraacetic acid disodium (EDTA) was added to give a final concentration of 0.005 M. The mixture was then gassed with nitrogen, and allowed to incubate with stirring using a "V" shaped stir bar in a sealed screw cap plastic conical reaction vessel (total container volume 1.5 ml) for at least 45 minutes, but no more than 120 minutes, at room temperature. In the Thioether protocol, the KLH was treated with TCEP, and separated using a P6DG column (Bio-Rad). The m-HGP-30 peptide and KLH were allowed to incubate for 18 hours to allow conjugation to occur. Then the reaction mixture was exhaustively dialyzed against 3–4 changes of 1 L each of PBS over 3–5 days and the product sterile filtered.

The final products, the peptide, peptide-KLH were analyzed for protein or peptide using the BCA protein assay, and adjusted to contain between 100–300 $\mu$g/ml of total protein or peptide, and stored frozen (−20° C.) in 1.5 ml aliquots.

III. Immunization, Anti-sera Collection and Processing

In a series of experiments, groups (5–10 per group) of 10–16 week old BALB/c female mice (Taconic Farms, Germantown, N.Y.) were immunized and test bled according to the following schedule. Schedule A immunization on day 0, day 7, test bleeding on days 14, 28 and 42.

The antigens were prepared with adjuvants as follows. The antigens were emulsified as described (Zimmerman et al 1996a,b Vaccine Res. 5:91, 5:103) for Incomplete Freund's adjuvant (Life Technology, Gaithersburg Md.) supplemented with Muramyl Dipeptide (Pierce). Other adjuvants, used included alum (Pierce, Gensia Pharmaceuticals, San Diego, Calif.), Ribi (Imunochem Research Inc., Hamilton, Mont.) and a proprietary product, Novasomes (Novavax, Rockville Md.) were used with antigen according to the manufactures's direction. The Novasome adjuvant was evaluated with or without a Lipid A supplement (Ribi).

Unanesthetized mice were placed in the palm of one hand with the nape held between the thumb and forefinger, and the little finger wrapped around the lower abdomen. The mice were inoculated with 0.2–0.4 ml of the inoculum equally divided between a subcutaneous site in the nape of the neck and intraperitonealy in the lower abdomen (Schedule B) or in the nape only (Schedule A). The inoculum contained 25.0 $\mu$g/animal of inoculation of the antigenic peptide.

The mice were anesthetized by Metofane™ Pitman-Moore (Mundelein, Ill.) for retrorbital bleeding and ear tagging. Blood from individual mice on the specified days was collected from the retrorbital vein using a 5¾" glass pasteur pipette, transferred to 1.5 ml centrifuge tube and allowed to clot. The clots were separated from the walls of the tube, and the cells/and clot separated by centrifugation from the sera. The sera from individual animals were collected and placed in labeled storage vials and stored frozen until ready for testing. At the first time of blood collection, each mouse was also ear tagged for identification purposes with an aluminum band imprinted with a unique sequential number (National Band and Tag, Lexington, Ky.).

IV. ELISA Assays

The sera was tested for the presence of antibody by an indirect ELISA. In this procedure, high binding plates (Maxi Sorb; Nunc, Naperville, Ill.) were used. The plates were coated at 4° C. with the HGP-30 (SEQ ID NO:1) or modified HGP-30 (SEQ ID NO:5) or a control peptide at a concentration of 1.0 $\mu$g/ml in 0.15 M bicarbonate coating buffer (pH 9.6) using 118 $\mu$l/well, and stored at 4° C. for 1–7 days. The control peptide was a twenty amino acid peptide from the V-3 loop of the env protein gp120. Other control peptides are well known to those skilled in the art for the purpose of detecting background and non-specific antibody. Prior to use, the wells were washed at least 2 times with PBS containing 0.05% Tween™ 20 (PBSTw), blocked with 150 $\mu$l of 0.2% bovine serum albumin (BSA) (Sigma Chemicals (St Louis, Mo.)) in PBSTw for 15–30 minutes, and washed at least two more times with PBSTw. Antibodies to the coating HGP-30, modified HGP-30 or a control peptide in the sample were assayed as follows.

First, an appropriate dilution, usually from 1:100 to 1:10,000 of the test antisera was made in 0.2% BSA in PBSTw, and 100 $\mu$l thereof was added per well. After all of the wells were loaded, the plates were sealed with an adhesive plate sealer (ICN, Costa Mesa, Calif.), and incubated for 2 hours at 37° C. The plates were then washed at least three times with PBSTw (>250 μl/well per wash), and drained. The wells were loaded with 100 μl of a dilution, usually 1:5000, in 5.0% BSA in PBSTw, of the enzyme-antibody conjugate, HRP-goat anti-murine immunoglobulins (Kirkegaard and Perry Laboratories (KPL), Gaithersburg, Md.). The plates were incubated for 1.5 hours with the enzyme-antibody conjugate before a final series of three washing steps and color development using, as the substrate, 100 μl/well of o-phenylenediamine dihydrochloride (OPD (Sigma)). The substrate was prepared by dissolving a 5.0 mg tablet in 12.5 ml of urea hydrogen peroxide phosphate citrate buffer (pH 5.0). The color reaction was stopped after about 60 minutes with 100 μl of 4.0 N H2SO4, and the color was read at 490 nanometers on an ELISA plate reader. Data was printed out and also saved on the hard drive and floppy disc for use in further analysis. Data points were collected in duplicates, and the values reported herein are the average.

As discussed below, in some cases, the second incubation (1.5 hours) was carried out with isotyping antisera of Goat anti-murine heavy chain specific class or subclass (μ, α, γ1, 2a, 2b and 3) (Sigma or ICN), and then an enzyme conjugate, HRP-rabbit-anti-goat immunoglobulins (KPL), was used before the substrate color development step.

EXAMPLE 1

Example 1 shows the antibody response after 28 days immunization on days 0 and 7 with 25 μg of HGP-30 peptide (SEQ ID NO:1) or m-HGP-30 (SEQ ID NO:5) either conjugated or unconjugated. The antigen used was evaluated with two adjuvants i) alum and ii) experimental adjuvant, Novosomes, which was being evaluated at the same time but with or without Lipid A. Novosomes are considered to overcome the need for conjugation of peptides to large proteins such as KLH. The KLH used in these experiments is one that is prepared under GMP conditions. The antibody response was measured as an indicator of immunological responses rather than as a measure of a specific CMI. The assay included the use of a control well coated with unrelated peptide; this insures that the signal indicating the binding of antibody is due to specific antibody and not some non-specific responses. This control value is subtracted from the value observed with the HGP-30 or m-HGP-30 coated wells. As expected and, as can be seen from the resulting data, the use of an adjuvant for this peptide is required and it appears as if the Novavax adjuvant (Novosomes) is not as potent as the approved Alum. This is true with both HGP-30 and a modified HGP-30 preparation. As is done elsewhere unless otherwise stated the sera were tested at a 1/200 dilution.

TABLE 1

Antibody response to HGP-30, Modified HGP-30 and HGP-30 KLH conjugates with either Alum or Novasomes as adjuvants

| Group | Number of animals | Number of responders |
|---|---|---|
| Novosomes + m-HGP-30 | 7 | 0 |
| Novosomes + m-HGP-30 with Lipid A | 7 | 0 |
| Novosomes + HGP-30 | 7 | 0 |
| Novosomes + HGP-30 with Lipid A | 7 | 0 |
| Novosomes + HGP-30-KLH | 6 | 6 |
| Novosomes + HGP-30-KLH with Lipid A | 5 | 5 |
| Alum + m-HGP-30 | 6 | 0 |
| Alum + HGP-30 | 6 | 0 |

EXAMPLE 2

In this example the alum adjuvant is evaluated using several preparations of KLH conjugates as shown in Table 2. In this case the alum was a preparation from Gensia and was approved for human use. An alum control groups was also evaluated at the same time. The HGP-30-KLH preparations II and V were prepared using CalBioChem and Pierce KLH (respectively) prepared by the glutaraldehyde method using the same HGP-30 material that was used in the previous Table 1 (Naylor et al 1991, Proc. Nat Acad Sci 84:2951). Notice that the number of responding mice and the signal at any particular dilution between the groups are comparable, as are the titers. This same KLH preparation from Pierce was used to prepare other conjugates by a different method, i.e., using 1-ethyl-3-(dimethyl aminopropyl)carbodiimide (EDC) (Williams, et al, 1981, Amer. Chem. Soc. 103:7090; Gilles, et al, 1990, Anal. Biochem., 184:244). It appears that this was not as good a preparation as the HGP-30 KLH made by using glutaraldehyde. Examination of the response to the modified HGP-30-KLH conjugate with the Pierce KLH prepared by the thioether method was more interesting. This m-HGP-30 peptide, which differs form HGP-30 by including 4 fewer amino acid residues from the carboxyl terminal region containing a B cell or antibody epitope and three additional residues at the amino terminus containing a T cell epitope, showed just as strong a signal. Indeed the titer seemed higher since as seen in Table 2 the dilutions were carried to three more steps in order to see a 50% drop in signal which was regarded as the titer.

TABLE 2

Use of Modified HGP-30 and HGP-30 KLH conjugates as immunogens with alum adjuvant: antibody titer

|  | Mouse number | "1/200 Control Peptide | Dilution Specific Peptide | Difference | "1/400 Control Peptide | Dilution Specific Peptide | Difference | "1/800 Control α Peptide | Dilution Specific a Peptide | Difference |
|---|---|---|---|---|---|---|---|---|---|---|
| I | 490 | 0.305 | 0.322 | 0.018 | 0.241 | 0.241 | 0.000 | 0.144 | 0.159 | 0.015 |
| Alum | 491 | 0.238 | 0.299 | 0.061 | 0.208 | 0.237 | 0.029 | 0.164 | 0.165 | 0.001 |
| Control | 492 | 0.271 | 0.320 | 0.049 | 0.245 | 0.242 | 0.000 | 0.159 | 0.162 | 0.003 |
|  | 493 | 0.300 | 0.319 | 0.020 | 0.241 | 0.245 | 0.005 | 0.163 | 0.165 | 0.002 |
|  | 494 | 0.314 | 0.330 | 0.017 | 0.258 | 0.259 | 0.001 | 0.177 | 0.184 | 0.008 |
|  | 495 | 0.352 | 0.357 | 0.005 | 0.240 | 0.242 | 0.002 | 0.161 | 0.161 | 0.000 |
|  | Group | Mean | "+/− SD | 0.028 | 0.022 |  | 0.006 | 0.012 | 0.005 | 0.006 |
| II | 456 | 0.217 | 1.133 | 0.916 | 0.191 | 0.962 | 0.771 | 0.133 | 0.696 | 0.563 |
| HGP-30 KLH | 457 | 0.268 | 1.243 | 0.975 | 0.199 | 0.943 | 0.745 | 0.149 | 0.652 | 0.504 |
| CalbioChem | 458 | 0.239 | 0.594 | 0.355 | 0.182 | 0.434 | 0.252 | 0.132 | 0.264 | 0.132 |
| Glutaraldehyde | 459 | 0.281 | 1.317 | 1.036 | 0.210 | 1.011 | 0.802 | 0.148 | 0.724 | 0.576 |
|  | 460 | 0.343 | 1.196 | 0.853 | 0.263 | 0.830 | 0.567 | 0.172 | 0.575 | 0.403 |
|  | 461 | 0.277 | 0.943 | 0.667 | 0.221 | 0.618 | 0.397 | 0.152 | 0.440 | 0.289 |
|  | 462 | 0.356 | 1.341 | 0.986 | 0.278 | 1.101 | 0.823 | 0.218 | 0.859 | 0.641 |
|  | Group | Mean | "+/− SD | 0.827 | 0.241 |  | 0.622 | 0.224 | 0.444 | 0.181 |
| III | 470 | 0.219 | 1.690 | 1.471 | 0.175 | 1.325 | 1.150 | 0.112 | 0.910 | 0.799 |
| m-HGP30-KLH | 471 | 0.321 | 1.304 | 0.983 | 0.162 | 1.033 | 0.871 | 0.124 | 0.648 | 0.524 |
|  | 472 | 0.263 | 1.440 | 1.177 | 0.174 | 1.268 | 1.094 | 0.111 | 0.842 | 0.731 |
|  | 474 | 0.233 | 1.923 | 1.690 | 0.107 | 1.651 | 1.544 | 0.077 | 1.193 | 1.116 |
|  | 475 | 0.195 | 1.929 | 1.734 | 0.115 | 1.805 | 1.690 | 0.088 | 1.245 | 1.157 |
|  | 476 | 0.301 | 2.192 | 1.891 | 0.229 | 1.853 | 1.624 | 0.135 | 1.422 | 1.288 |
|  | Group | Mean | "+/− SD | 1.491 | 0.351 |  | 1.329 | 0.335 | 0.936 | 0.295 |
| IV | 477 | 0.260 | 1.326 | 1.066 | 0.196 | 1.028 | 0.832 | 0.129 | 0.736 | 0.607 |
| HGP-30 KLH | 478 | 0.355 | 0.696 | 0.342 | 0.256 | 0.465 | 0.209 | 0.159 | 0.310 | 0.151 |
| Pierce EDC | 479 | 0.244 | 0.792 | 0.548 | 0.176 | 0.521 | 0.345 | 0.117 | 0.335 | 0.219 |
|  | 480 | 0.293 | 1.458 | 1.166 | 0.246 | 1.252 | 1.007 | 0.151 | 0.888 | 0.738 |
|  | 481 | 0.326 | 0.641 | 0.315 | 0.267 | 0.461 | 0.195 | 0.197 | 0.281 | 0.085 |
|  | 482 | 0.313 | 0.569 | 0.256 | 0.252 | 0.384 | 0.133 | 0.163 | 0.249 | 0.086 |
|  | Group | Mean | "+/− SD | 0.615 | 0.401 |  | 0.453 | 0.372 | 0.314 | 0.285 |
| V | 483 | 0.306 | 1.328 | 1.022 | 0.230 | 1.076 | 0.846 | 0.165 | 0.797 | 0.632 |
| HGP-30 KLH | 484 | 0.375 | 1.057 | 0.683 | 0.299 | 0.779 | 0.480 | 0.201 | 0.507 | 0.306 |
| Pierce | 485 | 0.291 | 0.970 | 0.680 | 0.206 | 0.759 | 0.553 | 0.139 | 0.461 | 0.322 |
| Glutaraldehyde | 486 | 0.327 | 1.326 | 0.999 | 0.253 | 1.080 | 0.828 | 0.174 | 0.752 | 0.578 |
|  | 487 | 0.287 | 1.217 | 0.931 | 0.209 | 0.858 | 0.649 | 0.156 | 0.597 | 0.441 |
|  | 488 | 0.358 | 1.476 | 1.118 | 0.267 | 1.218 | 0.952 | 0.180 | 0.816 | 0.637 |
|  | 489 | 0.294 | 0.680 | 0.386 | 0.200 | 0.406 | 0.206 | 0.138 | 0.233 | 0.095 |
|  | Group | Mean | "+/− SD | 0.831 | 0.258 |  | 0.645 | 0.257 | 0.430 | 0.202 |

EXAMPLE 3

Two different peptide variants of HGP-30 are used, which, while they contain 23 identical residues, also have minor but significant differences; an evaluation of the reactivity to each variant is desirable. Therefore, all reactive antisera against both HGP-30 preparations as shown in Table 3 are tested. surprisingly, it is observed that while with the standard HGP-30 KLH conjugates, resultant antisera, whether derived from Pierce or CalbioChem or BioSyn and whether conjugated by EDC or glutaraldehyde methods generate antibodies which recognize both HGP-30 preparations approximately equivalently. However, this was not as true for the modified HGP-30. It is apparent that while these IgG2a antibodies recognize the modified HGP-30 with the 4 amino acids deleted from the B cell terminus and addition of three amino acids extended into the CTL region of the adjacent p17 peptide HGP-35 they recognize less well the standard HGP-30. This may have major advantages as will be evident in the following example.

TABLE 3

Antisera derived by use of Modified HGP-30 and various HGP-30 KLH conjugates with alum adjuvant: nature of antibodies; nature of antigen specificity

| | | Specific antibody reactivity | | |
|---|---|---|---|---|
| GROUP | Mouse | HGP30 | M-HGP30 | M-HGP-30 |
| I- | 456 | | | |
|  | 457 | 0.085 | 0.072 | 0.850 |
|  | 459 | 0.888 | 0.698 | 0.790 |
|  | 461 | 0.879 | 0.458 | 0.520 |
|  | 462 | 0.119 | 0.130 | 1.090 |
|  | GROUP MEAN | 0.419 | 0.221 | 0.530 |
|  |  | 0.478 | 0.316 | 0.756 |
| II | 470 | | | |
|  | 472 | 0.228 | 0.919 | 4.040 |
|  | GROUP MEAN | 0.164 | 0.862 | 5.250 |
|  |  | 0.196 | 0.579 | 4.645 |
| III | 477 | | | |
|  | 478 | 0.508 | 0.495 | 0.970 |
|  | 479 | 0.242 | 0.000 | 0.000 |

TABLE 3-continued

Antisera derived by use of Modified HGP-30 and various HGP-30 KLH conjugates with alum adjuvant: nature of antibodies; nature of antigen specificity Specific antibody reactivity

| GROUP | Mouse | HGP30 | M-HGP30 | M-HGP-30 |
|---|---|---|---|---|
|  | 480 | 1.335 | 0.982 | 0.740 |
|  | GROUP MEAN | 0.356 0.610 | 0.060 0.384 | 0.170 0.470 |
| IV | 483 |  |  |  |
|  | 485 | 0.726 | 0.499 | 0.690 |
|  | 486 | 0.476 | 0.334 | 0.700 |
|  | 487 | 0.430 | 0.299 | 0.690 |
|  | 488 | 0.778 | 0.270 | 0.350 |
|  | GROUP MEAN | 0.217 0.525 | 0.078 0.296 | 0.360 0.558 |

EXAMPLE 4

TABLE 4

Isotypes distribution for anti HGP-30 antibodies using different KLH conjugates

|  | Mouse | IgG1 HGP30 SPECIFIC | IgG2a HGP30 SPECIFIC | IgG2b HGP30 SPECIFIC | IgG3 HGP30 SPECIFIC | IgM HGP30 SPECIFIC | IgGA HGP30 SPECIFIC |
|---|---|---|---|---|---|---|---|
| II | 456 | 1.837 | 0.124 | 0.270 | 0.025 | 0.100 | 0.000 |
|  | 457 | 1.611 | 0.026 | 0.155 | 0.017 | 0.000 | 0.000 |
|  | 459 | 1.777 | 0.098 | 0.277 | 0.034 | 0.058 | 0.000 |
|  | 460 | 1.541 | 0.503 | 0.216 | 0.052 | 0.000 | 0.016 |
|  | 461 | 1.339 | 0.107 | 0.014 | 0.000 | 0.000 | 0.008 |
|  | 462 | 1.703 | 0.299 | 0.388 | 0.000 | 0.060 | 0.009 |
| IV | 480 | 1.747 | 0.134 | 0.151 | 0.000 | 0.000 | 0.000 |
|  | 483 | 1.715 | 0.025 | 0.211 | 0.013 | 0.000 | 0.000 |
|  | 484 | 1.083 | 0.000 | 0.008 | 0.000 | 0.062 | 0.000 |
|  | 485 | 1.317 | 0.010 | 0.027 | 0.179 | 0.000 | 0.011 |
|  | 486 | 1.638 | 0.014 | 0.130 | 0.000 | 0.001 | 0.000 |
|  | 487 | 1.584 | 0.000 | 0.136 | 0.000 | 0.000 | 0.011 |
|  | 488 | 1.718 | 0.000 | 0.098 | 0.000 | 0.000 | 0.019 |
| III | 470 | 1.477 | 0.323 | 0.240 | 0.576 | 0.104 | 0.000 |
|  | 471 | 1.244 | 0.086 | 0.233 | 0.105 | 0.243 | 0.006 |
|  | 472 | 1.461 | 0.037 | 0.167 | 0.158 | 0.291 | 0.004 |
|  | 474 | 1.502 | 1.194 | 1.118 | 0.409 | 0.154 | 0.009 |
|  | 475 | 1.585 | 0.554 | 1.043 | 0.543 | 0.271 | 0.000 |
|  | 476 | 1.707 | 0.429 | 0.560 | 0.713 | 0.143 | 0.007 |

As can be seen from Table 4 the isotype of the antibodies from the KLH conjugates is dependent upon the source of the KLH used (i.e., from CalBioChem, Pierce, or Biosyn) and the nature of the peptide used. Note groups II and V both used HGP-30 conjugated to 2 different sources of KLH with the same method, while group IV used conjugated KLH via a different method. As can be readily appreciated, therefore, the use of a peptide (compare modified HGP-30 Group III to Groups II, IV and V) that favors the TH1 IgG2a (murine) or IgG3 (man) is highly advantageous.

This application is related to the commonly assigned copending application of the same inventors filed on even date herewith and titled, "Modified HGP-30 Heteroconjugate Peptides, Compositions and Methods of Use" and filed under attorney's docket no. CELL-102, and the disclosure of this copending application is incorporated herein by reference thereto.

What is claimed is:

1. A peptide having the formula of SEQ ID NO:2, SEQ ID NO:3, SEQ ID NO:4 OR SEQ ID NO:5 or a natural or spontaneous occurring allele thereof.

2. A peptide-carrier construct comprising the formula (I):

$$C^*\text{—}X\text{—}P^* \quad (I)$$

wherein

C* represents an immunogenic carrier material;

P* represents a peptide according to claim 1; and

X represents a direct bond or covalent linkage linking the immunogenic carrier material C* and the peptide P*.

3. A composition effective for eliciting an antibody response, when administered to a human patient in need thereof comprising peptide-carrier construct as set forth in claim 2 and an adjuvant.

4. A method for eliciting an antibody response in a human patient in need thereof, comprising administering to said patient an immunologically effective amount of an peptide-carrier construct as set forth in claim 2.

5. The method of claim 4 which further comprises administering the immunologically active peptide in combination with an immune response adjuvant.

6. A peptide according to claim 1 wherein the peptide is said natural or spontaneous occurring allele wherein the N-terminal thereof consists of the sequence of SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33 or SEQ ID NO:34.

7. A peptide according to claim 1 having the formula of SEQ ID NO:2, or a natural or spontaneous occurring allele thereof.

8. A peptide according to claim 1 having the formula of SEQ ID NO:3, or a natural or spontaneous occurring allele thereof.

9. A peptide according to claim 1 having the formula of SEQ ID NO:4, or a natural or spontaneous occurring allele thereof.

10. A peptide according to claim 1 having the formula of SEQ ID NO:5, or a natural or spontaneous occurring allele thereof.

11. A peptide-carrier construct comprising the formula (I):

$$C^*—X—P^* \qquad (I)$$

wherein
  C* represents an immunogenic carrier material;
  P* represents a peptide having SEQ ID NO:2, SEQ ID NO:3, SEQ ID NO:4 or SEQ ID NO:5; and
  X represents a direct bond or covalent linkage linking the immunogenic carrier material C* and the peptide P*.

12. A composition effective for eliciting an antibody response when administered to a human patient in need thereof comprising a peptide-carrier construct as set forth in claim 11 and an adjuvant.

13. A method for eliciting an antibody response in a human patient in need thereof comprising administering to said patient an immunologically effective amount of a peptide-carrier construct as set forth in claim 11.

14. The method of claim 13 which further comprises administering the peptide-carrier construct in combination with an adjuvant.

15. A peptide having SEQ ID NO:2.

16. A peptide having SEQ ID NO:3.

17. A peptide having SEQ ID NO:4.

18. A peptide having SEQ ID NO:5.

* * * * *

SEQUENCE LISTING (1) GENERAL INFORMATION:

(iii) NUMBER OF SEQUENCES:50

(2) INFORMATION FOR SEQ ID NO: 1:

(i) SEQUENCE CHARACTERISTICS:
      (A) LENGTH:30 amino acids
      (B) TYPE:amino acid
      (C) TOPOLOGY:linear (ii) MOLECULE TYPE:peptide (v) FRAGMENT TYPE:internal fragment (ix) FEATURE:
      (A) NAME/KEY:HGP-30
      (B) LOCATION:85 to 114
      (D) OTHER INFORMATION:fragment of p-17 gag protein of HIV (xi) SEQUENCE DESCRIPTION:SEQ ID NO:1:

```
Tyr Ser Val His Gln Arg Ile Asp Val Lys Asp Thr Lys Glu Ala Leu
            5                  10                  15

Glu Lys Ile Glu Glu Glu Gln Asn Lys Ser Lys Lys Lys Ala
            20                  25                  30
```

(2) INFORMATION FOR SEQ ID NO: 2:

(i) SEQUENCE CHARACTERISTICS:
      (A) LENGTH:25 amino acids
      (B) TYPE:amino acid
      (C) TOPOLOGY:linear (ii) MOLECULE TYPE:peptide (v) FRAGMENT TYPE:internal fragment (ix) FEATURE:
      (A) NAME/KEY:
      (B) LOCATION:82 to 106
      (D) OTHER INFORMATION:fragment of p-17 gag protein of HIV (xi) SEQUENCE DESCRIPTION:SEQ ID NO:2:

```
Ala Thr Leu Tyr Ser Val His Gln Arg Ile Asp Val Lys Asp Thr Lys
            5                  10                  15

Glu Ala Leu Glu Lys Ile Glu Glu Glu
            20                  25
```

(2) INFORMATION FOR SEQ ID NO: 3:

(i) SEQUENCE CHARACTERISTICS:
      (A) LENGTH:36 amino acids
      (B) TYPE:amino acid
      (C) TOPOLOGY:linear (ii) MOLECULE TYPE:peptide (v) FRAGMENT TYPE:internal fragment (ix) FEATURE:
      (A) NAME/KEY:
      (B) LOCATION:76 to 111
      (D) OTHER INFORMATION:fragment of p-17 gag protein of HIV (xi) SEQUENCE DESCRIPTION:SEQ ID NO: 3:

```
Ser Leu Tyr Asn Thr Val Ala Thr Leu Tyr Ser Val His Gln Arg Ile
            5                  10                  15
```

```
Asp Val Lys Asp Thr Lys Glu Ala Leu Glu Lys Ile Gln Glu Glu Gln
            20                  25                  30

Asn Lys Ser Lys
        35

(2) INFORMATION FOR SEQ ID NO: 4:

(i) SEQUENCE CHARACTERISTICS:
        (A) LENGTH:37 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 111
        (D) OTHER INFORMATION:fragment of p-17 gag protein of HIV (xi) SEQUENCE DESCRIPTION:SEQ ID NO: 4:

Arg Ser Leu Tyr Asn Thr Val Ala Thr Leu Tyr Ser Val His Gln Arg
            5                   10                  15

Ile Asp Val Lys Asp Thr Lys Glu Ala Leu Gln Lys Ile Glu Glu Glu
            20                  25                  30

Gln Asn Lys Ser Lys
        35

(2) INFORMATION FOR SEQ ID NO: 5:

(i) SEQUENCE CHARACTERISTICS:
        (A) LENGTH:29 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:82 to 110
        (B) LOCATION:
        (D) OTHER INFORMATION:fragment of p-17 gag protein of HIV (xi) SEQUENCE DESCRIPTION:SEQ ID NO: 5:

Ala Thr Leu Lys Ser Val His Gln Arg Ile Asp Val Lys Asp Thr Lys
            5                   10                  15

Glu Ala Leu Glu Lys Ile Glu Glu Glu Gln Asn Lys Ser
            20                  25

(2) INFORMATION FOR SEQ ID NO: 6:

(i) SEQUENCE CHARACTERISTICS:
        (A) LENGTH:37 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 111
        (D) OTHER INFORMATION:fragment of p-17 gag protein of HIV,
            CONSENSUS A (xi) SEQUENCE DESCRIPTION:SEQ ID NO: 6:
```

```
Lys Ser Leu Phe Asn Thr Val Ala Thr Leu Tyr Cys Val His Gln Arg
              5                  10                  15

Ile Asp Val Lys Asp Thr Lys Glu Ala Leu Asp Lys Ile Glu Glu Ile
             20                  25                  30

Gln Asn Lys Ser Lys
             35
```

(2) INFORMATION FOR SEQ ID NO: 7:

(i) SEQUENCE CHARACTERISTICS:
        (A) LENGTH:37 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 111
        (D) OTHER INFORMATION:fragment of p-17 gag protein of HIV,
            CONSENSUS B (xi) SEQUENCE DESCRIPTION:SEQ ID NO: 7:

```
Arg Ser Lys Tyr Asn Thr Val Ala Thr Leu Tyr Cys Val His Gln Arg
              5                  10                  15

Ile Glu Val Lys Asp Thr Lys Glu Ala Leu Asp Lys Ile Glu Glu Glu
             20                  25                  30

Gln Asn Lys Ser Lys
             35
```

(2) INFORMATION FOR SEQ ID NO: 8:

(i) SEQUENCE CHARACTERISTICS:
        (A) LENGTH:37 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 111
        (D) OTHER INFORMATION:fragment of p-17 protein of HIV,
            CONSENSUS C (xi) SEQUENCE DESCRIPTION:SEQ ID NO: 8:

```
Arg Ser Leu Xaa Asn Thr Val Ala Thr Leu Lys Cys Val His Xaa Xaa
              5                  10                  15

Ile Glu Val Arg Asp Thr Lys Glu Ala Leu Asp Lys Ile Glu Glu Glu
             20                  25                  30

Gln Asn Lys Xaa Gln
             35
```

(2) INFORMATION FOR SEQ ID NO: 9:

(i) SEQUENCE CHARACTERISTICS:
        (A) LENGTH:37 amino acids
        (B) TYPE:amino acid
        (C) TOPOLOGY:linear (ii) MOLECULE TYPE:peptide (v) FRAGMENT TYPE:internal fragment

```
        (ix) FEATURE:
              (A) NAME/KEY:
              (B) LOCATION:75 to 111
              (D) OTHER INFORMATION:fragment of p-17 protein of HIV,
                  CONSENSUS D (xi) SEQUENCE DESCRIPTION:SEQ ID NO: 9:

Lys Ser Leu Xaa Asn Thr Val Ala Thr Leu Tyr Cys Val His Glu Arg
                 5                  10                  15

Ile Glu Val Lys Asp Thr Lys Glu Ala Leu Glu Lys Met Glu Glu Glu
             20                  25                  30

Gln Asn Lys Ser Lys
             35

(2) INFORMATION FOR SEQ ID NO:10:

(i) SEQUENCE CHARACTERISTICS:
              (A) LENGTH:37 amino acids
              (B) TYPE:amino acid
              (C) TOPOLOGY:linear (ii) MOLECULE TYPE:peptide (v) FRAGMENT TYPE:internal fragment (ix) FEATURE:
              (A) NAME/KEY:
              (B) LOCATION:75 to 111
              (D) OTHER INFORMATION:fragment of p-17 protein of HIV,
                  CONSENSUS F (xi) SEQUENCE DESCRIPTION:SEQ ID NO:10:

Arg Ser Leu Xaa Asn Thr Val Xaa Val Leu Tyr Phe Val His Gln Arg
                 5                  10                  15

Val Glu Xaa Lys Asp Thr Lys Glu Ala Leu Glu Glu Val Glu Lys Ala
             20                  25                  30

Gln Lys Gln Gln Lys
             35

(2) INFORMATION FOR SEQ ID NO:11:

(i) SEQUENCE CHARACTERISTICS:
              (A) LENGTH:37 amino acids
              (B) TYPE:amino acid
              (C) TOPOLOGY:linear (ii) MOLECULE TYPE:peptide (v) FRAGMENT TYPE:internal fragment (ix) FEATURE:
              (A) NAME/KEY:
              (B) LOCATION:75 to 111
              (D) OTHER INFORMATION:fragment of p-17 protein of HIV,
                  CONSENSUS G (xi) SEQUENCE DESCRIPTION:SEQ ID NO:11:

Lys Ser Leu Xaa Asn Xaa Xaa Ala Xaa Leu Xaa Cys Xaa His Gln Arg
                 5                  10                  15

Ile Xaa Val Lys Asp Thr Lys Glu Ala Leu Glu Glu Val Glu Lys Ala
             20                  25                  30

Gln Lys Asn Ser Lys
             35

(2) INFORMATION FOR SEQ ID NO:12:

(i) SEQUENCE CHARACTERISTICS:
```

(A) LENGTH:37 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:75 to 111
            (D) OTHER INFORMATION:fragment of p-17 protein of HIV,
                CONSENSUS H (xi) SEQUENCE DESCRIPTION:SEQ ID NO:12:

Gln Ser Leu Phe Asn Leu Leu Ala Xaa Leu Tyr Cys Val His Gln Arg
                5                   10                  15

Ile Asp Xaa Lys Asp Thr Lys Glu Ala Leu Xaa Lys Xaa Xaa Glu Gln
            20                  25                  30

Asn Xaa Gln Xaa Xaa
            35

(2) INFORMATION FOR SEQ ID NO:13:

(i) SEQUENCE CHARACTERISTICS:
            (A) LENGTH:37 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:75 to 111
            (D) OTHER INFORMATION:fragment of p-17 protein of HIV,
                CONSENSUS O (xi) SEQUENCE DESCRIPTION:SEQ ID NO:13:

Xaa Ser Leu Trp Asn Ala Ile Xaa Val Leu Trp Cys Val His Asn Arg
                5                   10                  15

Xaa Xaa Ile Xaa Asp Thr Gln Gln Ala Ile Gln Lys Leu Lys Glu Val
            20                  25                  30

Met Xaa Lys Ser Ala
            35

(2) INFORMATION FOR SEQ ID NO:14:

(i) SEQUENCE CHARACTERISTICS:
            (A) LENGTH:20 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:75 to 94
            (D) OTHER INFORMATION:fragment of p-17 gag protein of
                HIV-1U455

(xi) SEQUENCE DESCRIPTION:SEQ ID NO:14:

Arg Ser Leu Tyr Asn Thr Val Ala Val Leu Tyr Cys Val His Gln Arg
                5                   10                  15

Ile Asp Val Lys
            20

(2) INFORMATION FOR SEQ ID NO:15:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1MAL (xi) SEQUENCE DESCRIPTION:SEQ ID NO:15:

Lys Ser Leu Tyr Asn Thr Val Ala Gly Leu Tyr Cys Val His Gln Arg
             5                   10                15

Ile Asp Val Lys
        20

(2) INFORMATION FOR SEQ ID NO:16:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1TN243

(xi) SEQUENCE DESCRIPTION:SEQ ID NO:16:

Lys Ser Leu Phe Asn Thr Val Ala Thr Leu Trp Cys Val His Gln Arg
             5                   10                15

Ile Glu Val Lys
        20

(2) INFORMATION FOR SEQ ID NO:17:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1SF2

(xi) SEQUENCE DESCRIPTION:SEQ ID NO:17:

Arg Ser Leu Tyr Asn Thr Val Ala Thr Leu Tyr Cys Val His Gln Arg
             5                   10                15

Ile Asp Val Lys
        20

(2) INFORMATION FOR SEQ ID NO:18:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1TB132

(xi) SEQUENCE DESCRIPTION:SEQ ID NO:18:

Arg Ser Leu Tyr Asn Thr Ile Ala Val Leu Tyr Cys Val His Gln Lys
            5                  10               15

Ile Glu Val Lys
        20

(2) INFORMATION FOR SEQ ID NO:19:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1LAI (xi) SEQUENCE DESCRIPTION:SEQ ID NO:19:

Arg Ser Leu Tyr Asn Thr Val Ala Thr Leu Tyr Cys Val His Gln Arg
            5                  10               15

Ile Glu Ile Lys
        20

(2) INFORMATION FOR SEQ ID NO:20:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1HXB2R (xi) SEQUENCE DESCRIPTION:SEQ ID NO:20:

Arg Ser Leu Tyr Asn Thr Val Ala Thr Leu Tyr Cys Val His Gln Arg
            5                  10               15

Ile Glu Ile Lys
        20

```
(2) INFORMATION FOR SEQ ID NO:21:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1MN (xi) SEQUENCE DESCRIPTION:SEQ ID NO:21:

Lys Ser Leu Tyr Asn Thr Val Ala Thr Leu Tyr Cys Val His Gln Lys
                5                   10                  15

Ile Glu Ile Lys
            20

(2) INFORMATION FOR SEQ ID NO:22:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1JH3

(xi) SEQUENCE DESCRIPTION:SEQ ID NO:22:

Lys Ser Leu Phe Asn Thr Val Ala Thr Leu Tyr Cys Val His Gln Arg
                5                   10                  15

Ile Glu Val Lys
            20

(2) INFORMATION FOR SEQ ID NO:23:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1JRCSF (xi) SEQUENCE DESCRIPTION:SEQ ID NO:23:

Thr Ser Leu Tyr Asn Thr Val Ala Thr Leu Tyr Cys Val His Gln Arg
                5                   10                  15

Ile Glu Ile Lys
            20

(2) INFORMATION FOR SEQ ID NO:24:
```

```
    (i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1DYI (xi) SEQUENCE DESCRIPTION:SEQ ID NO:24:

Arg Ser Leu Tyr Asn Thr Val Ala Thr Leu Tyr Cys Val His Gln Lys
            5                   10                  15

Ile Glu Val Lys
        20

(2) INFORMATION FOR SEQ ID NO:25:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:   fragment of p-17 gag protein of
            HIV-1NY5CG (xi) SEQUENCE DESCRIPTION:SEQ ID NO:25:

Arg Ser Leu Phe Asn Thr Val Ala Val Leu Tyr Cys Val His Gln Arg
            5                   10                  15

Ile Asp Val Lys
        20

(2) INFORMATION FOR SEQ ID NO:26:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1NL43

(xi) SEQUENCE DESCRIPTION:SEQ ID NO:26:

Arg Ser Leu Tyr Asn Thr Ile Ala Val Leu Tyr Cys Val His Gln Arg
            5                   10                  15

Ile Glu Val Lys
        20

(2) INFORMATION FOR SEQ ID NO:27:
```

```
    (i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:75 to 94
        (B) LOCATION:
        (D) OTHER INFORMATION:fragment of p-17 protein of
            HIV-1CDC4

(xi) SEQUENCE DESCRIPTION:SEQ ID NO:27:

Arg Ser Leu Tyr Asn Thr Val Ala Thr Leu Tyr Cys Val His Gln Arg
                 5                  10                  15

Ile Glu Val Arg
            20

(2) INFORMATION FOR SEQ ID NO:28:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1HAN (xi) SEQUENCE DESCRIPTION:SEQ ID NO:28:

Arg Ser Leu Tyr Asn Thr Val Ala Thr Leu Tyr Cys Val His Gln Lys
                 5                  10                  15

Ile Glu Val Lys
            20

(2) INFORMATION FOR SEQ ID NO:29:

(i) SEQUENCE CHARACTERISTICS:
        (A) LENGTH:20 amino acids
        (B) TYPE:amino acid
        (C) TOPOLOGY:linear (ii) MOLECULE TYPE:peptide (v) FRAGMENT TYPE:internal fragment (ix) FEATURE:
        (A) NAME/KEY:
        (B) LOCATION:75 to 94
        (D) OTHER INFORMATION:fragment of p-17 gag protein of
            HIV-1CAM1

(xi) SEQUENCE DESCRIPTION:SEQ ID NO:29:

Arg Ser Leu Tyr Asn Thr Val Ala Thr Leu Tyr Cys Val His Gln Lys
                 5                  10                  15

Ile Asp Lys Val
            20

(2) INFORMATION FOR SEQ ID NO:30:

(i) SEQUENCE CHARACTERISTICS:
```

(A) LENGTH:20 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:75 to 94
            (D) OTHER INFORMATION:fragment of p-17 gag protein of
                HIV-1RF (xi) SEQUENCE DESCRIPTION:SEQ ID NO:30:

Lys Ser Leu Tyr Asn Ala Val Ala Thr Leu Tyr Cys Val His Gln Asn
                5                  10                  15

Ile Glu Val Arg
            20

(2) INFORMATION FOR SEQ ID NO:31:

(i) SEQUENCE CHARACTERISTICS:
            (A) LENGTH:20 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:75 to 94
            (D) OTHER INFORMATION:fragment of p-17 gag protein of
                HIV-1D31

(xi) SEQUENCE DESCRIPTION:SEQ ID NO:31:

Arg Ser Leu Phe Asn Thr Val Ala Thr Leu Tyr Cys Val His Gln Arg
                5                  10                  15

Ile Glu Ile Lys
            20

(2) INFORMATION FOR SEQ ID NO:32:

(i) SEQUENCE CHARACTERISTICS:
            (A) LENGTH:20 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:75 to 94
            (D) OTHER INFORMATION:fragment of p-17 gag protein of
                HIV-1BH102

(xi) SEQUENCE DESCRIPTION:SEQ ID NO:32:

Arg Ser Leu Thr Asn Thr Val Ala Thr Leu Tyr Cys Val His Gln Arg
                5                  10                  15

Ile Glu Ile Lys
            20

(2) INFORMATION FOR SEQ ID NO:33:

(i) SEQUENCE CHARACTERISTICS:
            (A) LENGTH:20 amino acids
            (B) TYPE:amino acid

```
            (C) TOPOLOGY:linear (ii) MOLECULE TYPE:peptide (v) FRAGMENT TYPE:internal fragment (ix) FEATURE:
         (A) NAME/KEY:
         (B) LOCATION:75 to 94
         (D) OTHER INFORMATION:fragment of p-17 gag protein of
             HIV-1PV22

(xi) SEQUENCE DESCRIPTION:SEQ ID NO:33:

Arg Ser Leu Tyr Asn Thr Val Ala Thr Leu Tyr Cys Val His Gln Arg
                5                  10                  15

Ile Glu Ile Lys
            20

(2) INFORMATION FOR SEQ ID NO:34:

(i) SEQUENCE CHARACTERISTICS:
         (A) LENGTH:20 amino acids
         (B) TYPE:amino acid
         (C) TOPOLOGY:linear (ii) MOLECULE TYPE:peptide (v) FRAGMENT TYPE:internal fragment (ix) FEATURE:
         (A) NAME/KEY:
         (B) LOCATION:75 to 94
         (D) OTHER INFORMATION:fragment of p-17 gag protein of
             HIV-1JRFL (xi) SEQUENCE DESCRIPTION:SEQ ID NO:34:

Arg Ser Leu Tyr Asn Thr Val Ala Thr Leu Tyr Cys Val His Gln Arg
                5                  10                  15

Ile Glu Val Lys
            20

(2) INFORMATION FOR SEQ ID NO:35:

(i) SEQUENCE CHARACTERISTICS:
         (A) LENGTH:20 amino acids
         (B) TYPE:amino acid
         (C) TOPOLOGY:linear (ii) MOLECULE TYPE:peptide (v) FRAGMENT TYPE:internal fragment (ix) FEATURE:
         (A) NAME/KEY:
         (B) LOCATION:75 to 94
         (D) OTHER INFORMATION:fragment of p-17 gag protein of
             HIV-1ZAM18

(xi) SEQUENCE DESCRIPTION:SEQ ID NO:35:

Lys Ser Leu Phe Asn Thr Val Val Thr Leu Trp Cys Val His Glu Asp
                5                  10                  15

Ile Thr Val Arg
            20

(2) INFORMATION FOR SEQ ID NO:36:

(i) SEQUENCE CHARACTERISTICS:
         (A) LENGTH:20 amino acids
         (B) TYPE:amino acid
         (C) TOPOLOGY:linear
```

```
        (ii) MOLECULE TYPE:peptide (v) FRAGMENT TYPE:internal fragment (ix) FEATURE:
             (A) NAME/KEY:
             (B) LOCATION:75 to 94
             (D) OTHER INFORMATION:fragment of p-17 gag protein of
                 HIV-12AM19

(xi) SEQUENCE DESCRIPTION:SEQ ID NO:36:

Lys Ser Leu His Asn Ala Val Ala Val Leu Tyr Cys Val His Lys Xaa
                5                   10                  15

Ile Thr Val Arg
            20

(2) INFORMATION FOR SEQ ID NO:37:

(i) SEQUENCE CHARACTERISTICS:
             (A) LENGTH:20 amino acids
             (B) TYPE:amino acid
             (C) TOPOLOGY:linear (ii) MOLECULE TYPE:peptide (v) FRAGMENT TYPE:internal fragment (ix) FEATURE:
             (A) NAME/KEY:
             (B) LOCATION:75 to 94
             (D) OTHER INFORMATION:fragment of p-17 gag protein of
                 HIV-1ZAM20

(xi) SEQUENCE DESCRIPTION:SEQ ID NO:37:

Arg Ser Leu Tyr Asn Thr Val Ala Thr Lys Tyr Cys Val His Ala Gly
                5                   10                  15

Ile Glu Val Arg
            20

(2) INFORMATION FOR SEQ ID NO:38:

(i) SEQUENCE CHARACTERISTICS:
             (A) LENGTH:20 amino acids
             (B) TYPE:amino acid
             (C) TOPOLOGY:linear (ii) MOLECULE TYPE:peptide (v) FRAGMENT TYPE:internal fragment (ix) FEATURE:
             (A) NAME/KEY:
             (B) LOCATION:75 to 94
             (D) OTHER INFORMATION:fragment of p-17 gag protein of
                 HIV-1EII (xi) SEQUENCE DESCRIPTION:SEQ ID NO:38:

Arg Ser Leu Tyr Asn Thr Val Ala Thr Lys Tyr Cys Val His Lys Gly
                5                   10                  15

Ile Asp Val Lys
            20

(2) INFORMATION FOR SEQ ID NO:39:

(i) SEQUENCE CHARACTERISTICS:
             (A) LENGTH:20 amino acids
             (B) TYPE:amino acid
             (C) TOPOLOGY:linear
```

```
    (ii) MOLECULE TYPE:peptide (v) FRAGMENT TYPE:internal fragment (ix) FEATURE:
         (A) NAME/KEY:
         (B) LOCATION:75 to 94
         (D) OTHER INFORMATION:fragment of p-17 gag protein of
             HIV-1ZUZ6

(xi) SEQUENCE DESCRIPTION:SEQ ID NO:39:

Arg Ser Leu Phe Asn Thr Val Ala Thr Lys Tyr Cys Val His Glu Arg
                5                  10                  15

Ile Glu Val Lys
            20

(2) INFORMATION FOR SEQ ID NO:40:

(i) SEQUENCE CHARACTERISTICS:
         (A) LENGTH:20 amino acids
         (B) TYPE:amino acid
         (C) TOPOLOGY:linear (ii) MOLECULE TYPE:peptide (v) FRAGMENT TYPE:internal fragment (ix) FEATURE:
         (A) NAME/KEY:
         (B) LOCATION:75 to 94
         (D) OTHER INFORMATION:fragment of p-17 gag protein of
             HIV-1NDK (xi) SEQUENCE DESCRIPTION:SEQ ID NO:40:

Arg Ser Leu Tyr Asn Thr Val Ala Thr Lys Tyr Cys Val His Glu Arg
                5                  10                  15

Ile Glu Val Lys
            20

(2) INFORMATION FOR SEQ ID NO:41:

(i) SEQUENCE CHARACTERISTICS:
         (A) LENGTH:30 amino acids
         (B) TYPE:amino acid
         (C) TOPOLOGY:linear (ii) MOLECULE TYPE:peptide (v) FRAGMENT TYPE:internal fragment (ix) FEATURE:
         (A) NAME/KEY:
         (B) LOCATION:85 to 114
         (D) OTHER INFORMATION:fragment of p-17 gag protein of HIV;
             Thailand-B (xi) SEQUENCE DESCRIPTION:SEQ ID NO:41:

Tyr Cys Val His Gln Lys Ile Glu Val Lys Asp Thr Lys Glu Ala Leu
                5                  10                  15

Glu Lys Ile Glu Glu Glu Gln Asn Lys Ser Lys Lys Ala
            20                  25                  30

(2) INFORMATION FOR SEQ ID NO:42:

(i) SEQUENCE CHARACTERISTICS:
         (A) LENGTH:30 amino acids
         (B) TYPE:amino acid
         (C) TOPOLOGY:linear (ii) MOLECULE TYPE:peptide
```

(v) FRAGMENT TYPE:internal fragment (ix) FEATURE:
            (A) NAME/KEY:
            (B) LOCATION:85 to 114
            (D) OTHER INFORMATION:fragment of p-17 gag protein of
                HIV; Thailand-NE (xi) SEQUENCE DESCRIPTION:SEQ ID NO:42:

Trp Cys Val His Gln Arg Ile Glu Val Lys Asp Thr Lys Glu Ala Leu
                 5                  10                  15

Asp Lys Ile Glu Glu Val Gln Asn Lys Ser Gln Gln Lys Thr
             20                  25                  30

(2) INFORMATION FOR SEQ ID NO:43:

(i) SEQUENCE CHARACTERISTICS:
            (A) LENGTH:30 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:85 to 114
            (D) OTHER INFORMATION:fragment of p-17 gag protein of HIV;
                Uganda-A (xi) SEQUENCE DESCRIPTION:SEQ ID NO:43:

Tyr Cys Val His Gln Arg Ile Asp Val Lys Asp Thr Lys Glu Ala Leu
                 5                  10                  15

Asn Lys Ile Glu Glu Met Gln Asn Lys Asn Lys Gln Arg Thr
             20                  25                  30

(2) INFORMATION FOR SEQ ID NO:44:

(i) SEQUENCE CHARACTERISTICS:
            (A) LENGTH:30 amino acids
            (B) TYPE:amino acid
            (C) TOPOLOGY:linear (ii) MOLECULE TYPE:peptide (v) FRAGMENT TYPE:internal fragment (ix) FEATURE:
            (A) NAME/KEY:
            (B) LOCATION:85 to 114
            (D) OTHER INFORMATION:fragment of p-17 gag protein of HIV;
                Kenya-A (xi) SEQUENCE DESCRIPTION:SEQ ID NO:44:

Tyr Cys Val His Gln Arg Ile Asp Val Lys Asp Thr Lys Glu Ala Leu
                 5                  10                  15

Asp Lys Ile Glu Glu Ile Gln Asn Lys Ser Lys Gln Lys Thr
             20                  25                  30

(2) INFORMATION FOR SEQ ID NO:45:

(i) SEQUENCE CHARACTERISTICS:
            (A) LENGTH:30 amino acids
            (B) TYPE:amino acid
            (C) TOPOLOGY:linear (ii) MOLECULE TYPE:peptide (v) FRAGMENT TYPE:internal fragment (ix) FEATURE:
          (A) NAME/KEY:
          (B) LOCATION:85 to 114
          (D) OTHER INFORMATION:fragment of p-17 gag protein of HIV;
              Brazil-A/E (xi) SEQUENCE DESCRIPTION:SEQ ID NO:45:

Tyr Phe Val His Gln Arg Val Glu Val Lys Asp Thr Lys Glu Ala Leu
                 5                  10                  15

Asp Lys Leu Glu Glu Glu Gln Asn Lys Ser Gln Gln Lys Thr
             20                  25                  30

(2) INFORMATION FOR SEQ ID NO:46:

(i) SEQUENCE CHARACTERISTICS:
          (A) LENGTH:30 amino acids
          (B) TYPE:amino acid
          (C) TOPOLOGY:linear (ii) MOLECULE TYPE:peptide (v) FRAGMENT TYPE:internal fragment (ix) FEATURE:
          (A) NAME/KEY:
          (B) LOCATION:85 to 114
          (D) OTHER INFORMATION:fragment of p-17 gag protein of HIV;
              Brazil-B (xi) SEQUENCE DESCRIPTION:SEQ ID NO:46:

Tyr Cys Val His Gln Lys Ile Asp Val Arg Asp Thr Lys Glu Ala Leu
                 5                  10                  15

Glu Lys Val Glu Glu Glu Gln Asn Lys Ser Lys Glu Lys Ala
             20                  25                  30

(2) INFORMATION FOR SEQ ID NO:47:

(i) SEQUENCE CHARACTERISTICS:
          (A) LENGTH:30 amino acids
          (B) TYPE:amino acid
          (C) TOPOLOGY:linear (ii) MOLECULE TYPE:peptide (v) FRAGMENT TYPE:internal fragment (ix) FEATURE:
          (A) NAME/KEY:
          (B) LOCATION:85 to 114
          (D) OTHER INFORMATION:fragment of p-17 gag protein of HIV;
              Uganda-B (xi) SEQUENCE DESCRIPTION:SEQ ID NO:47:

Tyr Cys Val His Gln Arg Ile Asp Val Lys Asp Thr Lys Glu Ala Leu
                 5                  10                  15

Asp Lys Ile Glu Glu Glu Gln Asn Lys Ser Lys Lys Lys Glu
             20                  25                  30

(2) INFORMATION FOR SEQ ID NO:48:

(i) SEQUENCE CHARACTERISTICS:
          (A) LENGTH:30 amino acids
          (B) TYPE:amino acid
          (C) TOPOLOGY:linear (ii) MOLECULE TYPE:peptide (v) FRAGMENT TYPE:internal fragment

```
        (ix) FEATURE:
             (A) NAME/KEY:
             (B) LOCATION:85 to 114
             (D) OTHER INFORMATION:fragment of p-17 protein of HIV (xi) SEQUENCE DESCRIPTION:SEQ ID NO:48:

Tyr Cys Val His Lys Gly Ile Glu Val Arg Asp Thr Lys Glu Ala Leu
              5                   10                  15

Asp Lys Ile Glu Glu Glu Gln Asn Lys Ile Gln Gln Lys Thr
             20                  25                  30

(2) INFORMATION FOR SEQ ID NO:49:

(i) SEQUENCE CHARACTERISTICS:
             (A) LENGTH:30 amino acids
             (B) TYPE:amino acid
             (C) TOPOLOGY:linear (ii) MOLECULE TYPE:peptide (v) FRAGMENT TYPE:internal fragment (ix) FEATURE:
             (A) NAME/KEY:
             (B) LOCATION:85 to 114
             (D) OTHER INFORMATION:fragment of p-17 gag protein of HIV;
                 India-C (xi) SEQUENCE DESCRIPTION:SEQ ID NO:49:

Tyr Cys Val His Xaa Xaa Ile Glu Val Arg Asp Thr Lys Glu Ala Leu
              5                   10                  15

Asp Lys Ile Glu Glu Glu Gln Asn Lys Xaa Gln Gln Lys Thr
             20                  25                  30

(2) INFORMATION FOR SEQ ID NO:50:

(i) SEQUENCE CHARACTERISTICS:
             (A) LENGTH:30 amino acids
             (B) TYPE:amino acid
             (C) TOPOLOGY:linear (ii) MOLECULE TYPE:peptide (v) FRAGMENT TYPE:internal fragment (ix) FEATURE:
             (A) NAME/KEY:
             (B) LOCATION:85 to 114
             (D) OTHER INFORMATION:fragment of p-17 gag protein of HIV;
                 Uganda-D (xi) SEQUENCE DESCRIPTION:SEQ ID NO:50:

Tyr Cys Val His Glu Arg Ile Lys Val Ala Asp Thr Lys Glu Ala Leu
              5                   10                  15

Asp Lys Ile Glu Glu Gln Thr Lys Ser Lys Lys Ala
             20                  25                  30
```